(12) United States Patent
Gurewich et al.

(10) Patent No.: US 7,074,401 B2
(45) Date of Patent: Jul. 11, 2006

(54) METHODS, DEVICES, AND COMPOSITIONS FOR LYSIS OF OCCLUSIVE BLOOD CLOTS WHILE SPARING WOUND SEALING CLOTS

(75) Inventors: Victor Gurewich, Cambridge, MA (US); John N. Williams, Boston, MA (US); Jian-Ning Liu, Brighton, MA (US); Paolo Sarmientos, Lecco (IT); Massimiliano Pagani, Castelli Calepio (IT)

(73) Assignee: Thrombolytic Science, Inc., Boston, MA (US)

( * ) Notice: Subject to any disclaimer, the term of this patent is extended or adjusted under 35 U.S.C. 154(b) by 39 days.

(21) Appl. No.: 10/826,826

(22) Filed: Apr. 16, 2004

(65) Prior Publication Data

US 2005/0031607 A1    Feb. 10, 2005

Related U.S. Application Data

(60) Provisional application No. 60/464,003, filed on Apr. 18, 2003, provisional application No. 60/463,930, filed on Apr. 18, 2003, provisional application No. 60/464,002, filed on Apr. 18, 2003.

(51) Int. Cl.
*A61K 38/49* (2006.01)
*A61K 38/36* (2006.01)
*C12N 9/72* (2006.01)
*C12N 9/64* (2006.01)
*C07H 21/04* (2006.01)

(52) U.S. Cl. .................. 424/94.63; 435/215; 435/226; 514/12; 536/23.2

(58) Field of Classification Search ............. 424/94.63; 435/215, 226, 69.2; 536/23.2; 514/12
See application file for complete search history.

(56) References Cited

U.S. PATENT DOCUMENTS

| | | | |
|---|---|---|---|
| 5,472,692 A * | 12/1995 | Liu et al. ................. | 424/94.63 |
| 5,626,841 A | 5/1997 | Gurewich ................. | 424/94.63 |
| 5,759,542 A | 6/1998 | Gurewich ................. | 424/94.64 |
| 5,866,358 A | 2/1999 | Brandazza et al. ........ | 435/69.1 |
| 6,364,893 B1 | 4/2002 | Sahatjian et al. ........... | 606/194 |
| 6,409,716 B1 | 6/2002 | Sahatjian et al. ........... | 604/509 |
| 2002/0098179 A1* | 7/2002 | Brearley et al. ......... | 424/94.64 |
| 2002/0138858 A1* | 9/2002 | Pinsky ......................... | 800/8 |

OTHER PUBLICATIONS

Parsons et al., "Diffusion- and perfusion-weighted MRI response to thrombolysis in stroke," Ann Neurol 51(1):28-37, 2001.*

(Continued)

*Primary Examiner*—Robert A. Wax
*Assistant Examiner*—Rosanne Kosson
(74) *Attorney, Agent, or Firm*—Pierce Atwood LLP; Kevin M. Farrell

(57) ABSTRACT

It has now been discovered that certain mutant forms of pro-urokinase ("pro-UK"), such as so-called pro-UK mutant "M5" ($Lys^{300} \rightarrow His$), perform in the manner of pro-UK in lysing "bad" blood clots (those clots that occlude blood vessels), while sparing hemostatic fibrin in the so-called "good" blood clots (those clots that seal wounds, e.g., after surgery or other tissue injury). Thus, these pro-UK mutants are excellent and safe thrombolytic agents. These advantages allow them to be used in a variety of new methods, devices, and compositions useful for thrombolysis and treating various cardiovascular disorders in clinical situations where administration of other known thrombolytic agents has been too risky or even contraindicated.

6 Claims, 19 Drawing Sheets

Bleeding Time Before and During Clot Lysis in Dogs

OTHER PUBLICATIONS

Barnwell et al., "Safety and efficacy of delayed intraarterial urokinase therapy with mechanical clot disruption for thromboembolic stroke," Am J Neuroradiology, 15(10):1817-1822, 1994.*

Gurewich et al., "Effective and Fibrin-specific Clot Lysis by a Zymogen Precursor Form of Urokinase (Pro-urokinase)", J. Clin. Invest., vol. 73, pp. 1731-1739 (1984).

Heckel et al., "Prediction of the three-dimensional structure of the enzymatic domain of t-PA", J. Comp. Aided Mol. Des., vol. 2, pp. 7-14 (1988).

Liu et al., "A Comparative Study of the Promotion of Tissue Plasminogen Activator and Pro-Urokinase-induced Plasminogen Activation by Fragments D and E-2 of Fibrin", J. Clin. Invest., vol. 88, pp. 2012-2017 (1991).

Liu et al., "Inactivation of the Intrinsic Activity of Pro-urokinase by Diisoprophyl Fluorophosphate Is Reversible", The Journal of Biological Chemistry, vol. 270(15), pp. 8408-8410 (1995).

Liu et al., "Fragment E-2 from Fibrin Substantially Enhances Pro-urokinase-Induced Glu-Plasminogen Activation. A Kinetic Study Using the Plasmin-Resistant Mutant Pro-urokinase Ala-158-rpro-UK", Biochemistry, vol. 31, pp. 6311-6317 (1992).

Liu et al., Prourokinase Mutant That Induces Highly Effective Cost Lysis Without Interfering With Hemostatsis, Circulation Research, vol. 90, pp. 757-763 (2002).

Liu et al., "A Site-Directed Mutagenesis of Pro-Urokinase at the Flexiblr Loop Region of Active Domain", Advances in Gene Technology: Protein Engineering and Beyond, Abstract Only.

Nienaber et al., "Conformational Similarities between One-Chain and Two-Chain Tissue Plasminogen Activator (t-PA): Implications to the Activation Mechanism on One-Chain t-PA", Biochemistry, vol. 31, pp. 3852-3861 (1992).

Orsini et al., "Efficient renaturation and fibrinolytic properties of prourokinase and a deletion mutant expressed in *Escherichia coli* as inclusion bodies", Eur. J. Biochem., vol. 195, pp. 691-697 (1991).

Pannell et al., "Activation of Plasminogen by Single-Chain Urokinase or by Two-chain Urokinase—A Demonstration That Single-Chain Has a Low Catalytic Activity (Pro-Urokinase)", Blood, vol. 69(1), pp. 22-26 (1987).

Peterson et al., "Quenching of the Amidolytic Activity of One-Chain Tissue-Type Plasminogen Activator by Mutation of Lysine-416", Biochem., vol. 29, pp. 3451-3457 (1990).

Verde et al., "Identification and primary sequence of an unspliced human urokinase poly(A)$^+$RNA", Proc. Natl. Acad. Sci., vol. 81, pp. 4727-4731 (1984).

Notification of Transmittal of the International Search Report and Written Opinion of the International Searching Authority (and including the International Search Report and Written Opinion of the International Searching Authority ) mailed Apr. 5, 2005.

Yuming et al., "High-level Expression and Purification of Human Pro-UK cDNA in *Escherichia coli*", Chinese Journal of Biotechnology, vol. 13(4), pp. 233-238 (1998).

* cited by examiner

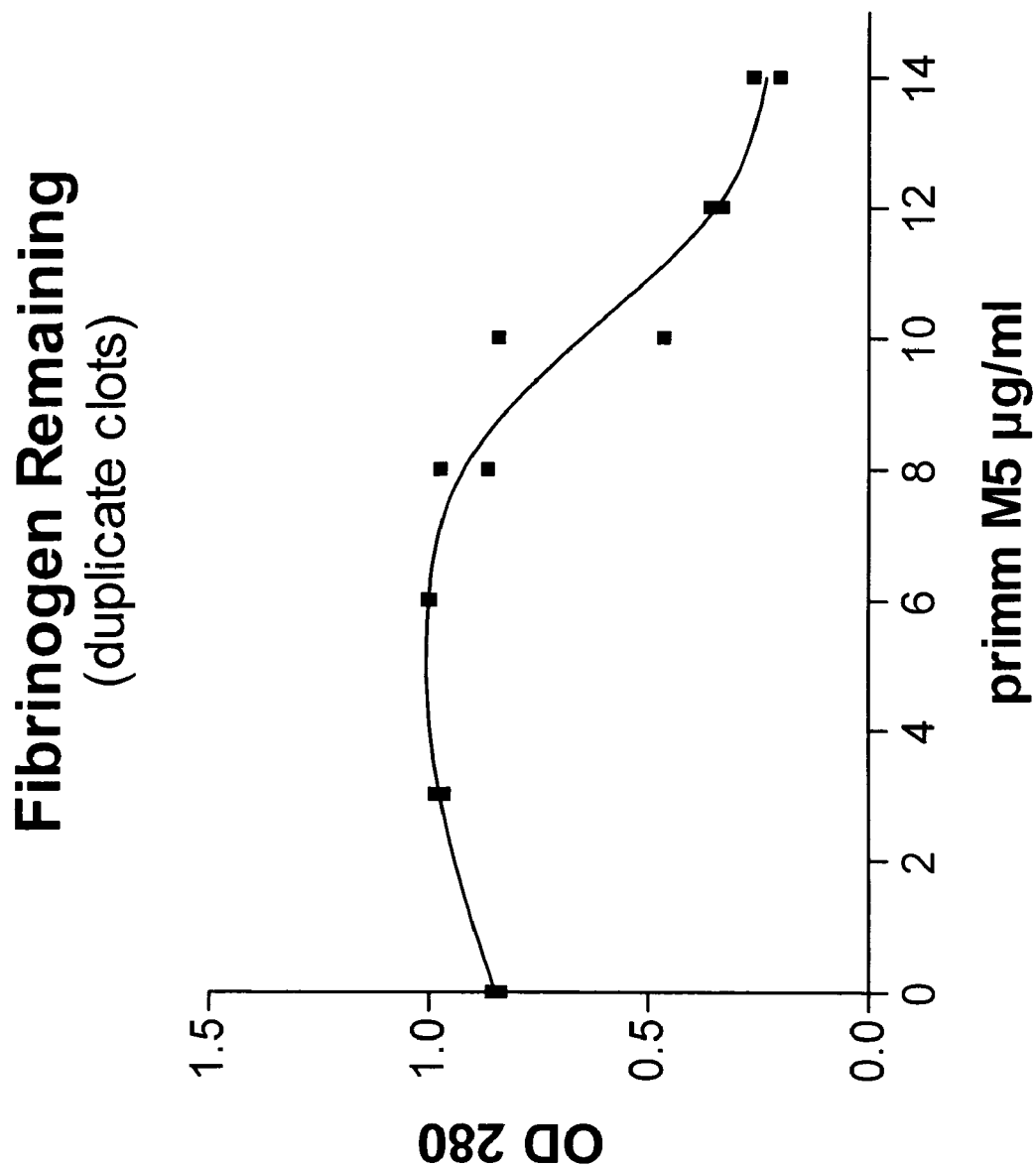

Construction of pET29-uPA(M5) expression plasmid

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
gaggattaca tatgagcaat gagc                                    24

<210> SEQ ID NO 2
<211> LENGTH: 33
<212> TYPE: DNA
<213> ORGANISM: Artificial Sequence -continued

```
<220> FEATURE:
<223> OTHER INFORMATION: Primer

<400> SEQUENCE: 2
ctggggaccg agctctcaga gggccaggcc att                              33

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
ggctttggac acgagaattc taccgactat ctc                              33

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
agaattctcg tgtccaaagc cagtgatctc ac                               32
```

METHODS, DEVICES, AND COMPOSITIONS FOR LYSIS OF OCCLUSIVE BLOOD CLOTS WHILE SPARING WOUND SEALING CLOTS

CROSS-REFERENCE TO RELATED APPLICATIONS

This application claims priority from U.S. Provisional Patent Application Ser. Nos. 60/464,003, 60/463,930, and 60/464,002, all filed on Apr. 18, 2003. The contents of each of these applications are incorporated herein by reference in their entirety.

TECHNICAL FIELD

The invention relates to the use of prourokinase mutants in various methods, devices, and compositions for therapeutic thrombolysis without inducing hemorrhage.

BACKGROUND

The leading two causes of death listed by the World Health Organization (1998) are coronary heart disease and cerebrovascular disease. Since these diseases are largely triggered by blood clots, there is a considerable need for safe and effective thrombolytic agents (drugs capable of dissolving clots and restoring blood flow). However, blood clots also perform the essential physiological function of preventing hemorrhage by sealing injured vessels. This process is called hemostasis and most thrombolytic drugs interfere with hemostasis by inducing a hemophilia-like state. More importantly, these drugs lyse hemostatic fibrin (which seals injuries). By these two mechanism, thrombolytic therapy has carried significant hemorrhagic risk.

When intravascular blood clotting occurs an occlusive clot or thrombus forms, and blood flow is often arrested at that site. Blood clots consist largely of fibrin, which is a natural polymer that forms from fibrinogen in blood as the end-product of clotting. Depending on the location in the arterial system, i.e., heart, brain, or leg, such a clot can trigger a heart attack, stroke, or peripheral gangrene. In the venous circulation the same process can cause thrombophlebitis (deep vein thrombosis) or pulmonary embolism (lung clots). Together, these cardiovascular diseases constitute the leading causes of death and disability in industrialized countries. Since the tendency to form occlusive clots increases with age and populations are getting older, the incidence of these disorders is increasing worldwide.

Not surprisingly, blood clotting and thrombolysis have been a major focus of biomedical research over the past 30 years, and this research has produced an array of anti-clotting (anticoagulant) as well as clot-dissolving (thrombolytic) drugs. The first thrombolytic drugs to be developed were streptokinase (SK) and urokinase (UK), both of which have certain shortcomings, e.g., SK is antigenic and has limited efficacy, and both SK and UK induce non-specific effects, since they do not target blood clots, and act systemically upon constituents of healthy blood, causing the hemophilia-like state referred to above.

Tissue plasminogen activator (t-PA) was developed some years later and was one of the first biotechnology products. T-PA is non-antigenic, since it is a natural enzyme, is clot-specific (less likely to cause the hemophilia-like state), and is almost twice as effective as SK in lysing blood clots in vitro. However, when t-PA was tested clinically, it was found to induce more hemorrhagic side effects, and be associated with a higher stroke and reocclusion rate than SK, despite its superior specificity. These and other side effects caused its clinical benefits in the treatment of heart attacks to be little better than those obtained with SK.

Another thrombolytic agent, pro-urokinase (pro-UK) is a natural zymogen that activates plasminogen, to form plasmin, which in turn activates pro-UK to UK. Like t-PA, pro-UK is known to be selective for plasminogen bound to blood clots (see, e.g., Husain et al., U.S. Pat. No. 4,381,346), in contrast to UK (or SK), which activates plasminogen indiscriminately. This is a problem because of the high concentration of plasminogen in blood. Thus, pro-UK is referred to as fibrin clot-specific, or selective, whereas UK is non-specific. Pro-UK seemed better adapted to pharmacological use than SK, UK, or t-PA, because it is substantially inert in the blood (being a pro-enzyme) at physiological concentrations. Its activation is dependent on the presence of a fibrin clot or thrombus. Unfortunately, at therapeutic doses, which are significantly larger than naturally occurring concentrations, pro-UK becomes unstable and is readily converted by plasmin to UK. When this occurs, the selective mechanism of action of pro-UK is lost, and the hemophilia-like side effects and bleeding take place.

Because of such shortcomings of presently available thrombolytic agents, heart attacks are currently treated with angioplasty and stents, despite their technical complexity, cost, and associated delay in treatment of the patient. Out of the 1 to 2 million heart attacks that occur in the U.S. and Europe annually, a growing percentage is being treated by these invasive procedures. This is because a number of studies have demonstrated that the clinical outcome is better than with the commercially available thrombolytic drugs, and there is no risk of bleeding or hemorrhagic stroke.

The only new thrombolytic drugs that have appeared on the market in the past five years are mutant forms of t-PA. These mutant t-PAs have an efficacy and side effects essentially identical to those of t-PA, but can be administered as a bolus injection rather than by an extended infusion. Like t-PA and SK, these drugs are inimical to angioplasty, which, when possible, has become the treatment of choice for most heart attacks. Therefore, coronary reperfusion is delayed until a patient is brought into an adequately staffed catheterization laboratory. This takes at least 60–90 minutes, a critical time during which significant heart muscle is permanently lost due to lack of blood supply (perfusion).

Mutant forms of pro-UK are described in Liu et al., U.S. Pat. No. 5,472,692. These pro-UK mutants are said to have lower intrinsic activity than pro-UK and are more stable in plasma than native pro-UK. The pro-UK mutants are said to be used and administered as thrombolytic agents.

SUMMARY

The invention is based, at least in part, on the discovery that certain mutant forms of pro-UK ("pro-UK mutants") such as pro-UK mutant "M5" (as defined herein), are plasminogen activators that spare "good" fibrin clots (the hemostatic fibrin that seals injured blood vessels), while at the same time lysing the "bad" clots (that occlude blood vessels). The hemostatic fibrin is also important for repair of spontaneous vessel injury, a particularly common event in the elderly. The invention is also based in part on the realization of the importance, in this connection, that the substrate for pro-UK and pro-UK mutants, plasminogen, has different conformations depending on whether it is bound to fibrin in an occlusive blood clot or a wound sealing blood clot. It is believed that this difference in conformation of plasminogen allows the pro-UK mutants to preferentially lyse the bad clots and spare the good clots. Furthermore, certain mutants such as M5, have about twice the fibrinolytic activity in a plasma milieu at fibrin-specific concentrations as pro-UK (or t-PA).

In general, in one aspect, the invention features methods of treating a person with symptoms of stroke by (a) determining that a person potentially has had a stroke based on symptoms of stroke, e.g., without the need for medical confirmation or a complete diagnosis; and (b) administering to the person a composition comprising an amount of a pro-UK mutant, e.g., a so-called "flexible loop" mutant such as M5, effective to lyse any potential blood clot causing the symptoms of stroke. In these methods, the composition can be administered more than 3 hours after the onset of symptoms, a bolus of the composition can be administered including 20–50 mg of the pro-UK mutant, and the methods can further include obtaining a medical confirmation of an occlusive thrombus in the brain (e.g., by CT scan), and administering an infusion of the composition at a pro-UK flexible loop mutant dosage of dose of 120–200 mg/hour (intravenous) or 50–100 mg/hour (intra-arterial).

A pro-UK flexible loop mutant is a polypeptide that has the amino acid sequence of wild-type pro-UK (which has 411 amino acids), but with one or more amino acids in the "flexible loop" (which includes the amino acids at locations 297–313) replaced by a neutral amino acid such as alanine (Ala) or an amino acid that can take on only a weak positive charge, such as histidine (His). These flexible loop mutants are described in U.S. Pat. No. 5,472,692. One example of a pro-UK flexible loop mutant is M5, which has the complete amino acid sequence of wild-type pro-UK, but with one amino acid alteration, $Lys^{300} \rightarrow His$.

Pro-UK flexible loop mutants "spare" wound sealing blood clots, which means that they cause lysis (via plasminogen) of fibrin in occlusive blood clots preferentially to the fibrin in wound sealing clots.

"Medical confirmation," refers to confirmation of an initial diagnosis based on a patient's symptoms (either observed by the physician or EMT, or described by the patient), by medical testing such as with medical devices, blood test, and the like.

In another aspect, the invention features methods of treating a person with symptoms of a heart attack by (a) diagnosing a patient as potentially having a heart attack based on symptoms of a heart attack, e.g., without the need for medical confirmation; and (b) administering to the potential heart attack patient a composition comprising an amount of a pro-urokinase mutant, e.g., a flexible loop mutant such as M5, effective to lyse any potential blood clot causing the symptoms of a heart attack. In these methods, the composition can be administered within 90 minutes of the onset of symptoms, and a bolus of the composition can be administered including 20–50 mg of the pro-UK mutant. In addition, the methods can further include obtaining a medical confirmation of an occlusive thrombus in a coronary artery, and administering an infusion of the composition at a pro-UK mutant dosage of 50–200 mg/hour.

As used herein, the term "diagnosing" refers to any observation of symptoms, such as symptoms of a potential stroke or heart attack, by any medical personnel, including doctors, nurses, emergency medical technicians ("EMTs"), physician's assistants, and the like, or even a lay person with some minimal medical training. The term "diagnosing" does not require a formal diagnosis made by a doctor, and the diagnosis can be made in the field, e.g., in the patient's home or other public place, or in a doctor's office or hospital.

In other embodiments, the invention features methods of lysing occlusive thrombi and emboli in a patient before, during, or after surgery, by administering to the patient a composition comprising an amount of a pro-UK mutant, e.g., a flexible loop mutant such as M5, effective to preferentially lyse any potential occlusive thrombus or embolus compared to hemostatic fibrin in wound sealing clots. In this method, the composition can be administered by infusion within about one, two, or three hours before or after (up to 24 hours after) surgery, or during surgery, and the composition can be administered by infusion at a pro-UK flexible loop mutant dosage of 50–200 mg/hour, or performing balloon angioplasty.

The invention also includes an intravascular expandable catheter for delivering to a vascular site in a patient an activated, two-chain pro-UK mutant, e.g., flexible loop mutant, ("mutant UK"). The catheter includes (a) a catheter body having proximal and distal ends; (b) an expandable portion arranged at the distal end of the catheter body; and (c) a carrier layer arranged on a surface of the expandable portion, wherein the carrier layer includes an amount of an activated pro-UK flexible loop mutant ("mutant UK") effective to lyse thrombi or emboli in contact with the expandable portion. In this catheter, the carrier layer can be a hydrogel selected to quickly release effective amounts of the mutant UK upon contact with a thrombus or embolus. The amount of mutant UK can be, e.g., 0.1–0.5 mg. The carrier layer can include a lumen containing the mutant UK and one or more apertures that are pressed against a thrombus or embolus to allow the thrombus or embolus to protrude into the one or more apertures, thereby contacting the mutant UK.

In certain embodiments, the carrier layer can be two-chain pro-UK mutant M5, e.g., low molecular weight two-chain M5, and the expandable portion can be an angioplasty balloon, or a stent-placement balloon.

In another aspect, the invention features an intravascular device, such as a stent or suture, for delivering to a vascular site in a patient a pro-urokinase ("pro-UK") flexible loop mutant ("mutant UK") that includes (a) a body; and (b) a carrier layer arranged on a surface of the body, wherein the carrier layer includes a sustained release agent that slowly releases over time an amount of a pro-UK flexible loop mutant effective to lyse thrombi or emboli in contact with the body.

The invention also features methods of clearing lumens of blood clots by obtaining a lumen that contains or may contain a blood clot; and flowing through the lumen a solution comprising an activated, two-chain pro-UK mutant ("mutant UK"), e.g., activated, two-chain flexible loop pro-UK mutant, such as M5, or low molecular weight, two-chain pro-UK mutant, such as M5, for a time sufficient for any blood clots to be dissolved, thereby clearing the lumen of blood clots. The methods can use a solution having a concentration of mutant UK of 0.05–0.2 mg. The lumen can be in a catheter, a blood pump, or in an artificial organ, such as a kidney machine.

The invention also relates to recombinant DNA methods of producing non-glycosylated, single-chain mutants (e.g., $Lys^{300} \rightarrow His$) of pro-UK. In general, the invention features methods of preparing a pro-UK mutant polypeptide by (a) obtaining a nucleic acid molecule that encodes a pro-UK mutant polypeptide; (b) inserting the nucleic acid molecule into a pET29a expression plasmid comprising a phage T7 promoter and Shine-Dalgarno sequence; (c) transforming E. coli type B strain bacteria BL21/DE3 RIL with the expression plasmid; (d) culturing the transformed bacteria for a time and under conditions sufficient to enable the bacteria to express pro-UK mutant polypeptide; and (e) isolating the pro-UK mutant polypeptide from the transformed bacteria.

Alternatively, one can obtain the required transformed bacteria, and follow the same culturing and isolation steps to obtain the pro-UK mutant polypeptide. In these methods, the pro-UK mutant can be a pro-UK flexible loop mutant, e.g., M5. The pro-UK mutant can be non-glycosylated and has a molecular weight of about 45,000 daltons.

In the new methods, the culturing can be a two-stage fermentation. For example, the first stage of fermentation can include adding to a flask a cell culture diluted in sterile EC1 medium and growing the culture at 34–37° C. overnight with agitation to form a seed culture, wherein the cell culture comprises a glycerol suspension of an LB culture of the transformed bacteria and containing a sufficient amount of kanamycin, e.g., 30 µg/ml.

The second stage of fermentation can include a) adding the seed culture to a fermentor; b) maintaining the pH in the fermentor at about 6.5 to 7.5, e.g., 6.8; c) maintaining the dissolved oxygen concentration in the culture medium at 35–45%, e.g., 40%, of air saturation; d) maintaining the temperature of fermentation at about 34–37° C.; and e) adding to the fermentor a nutrient feeding solution, comprising one or more sugars, when all glucose initially present in the fermentor at step a) is consumed, following the equation $V = V_o\ e^{0.18t}$, where V=volume of feeding solution added (ml/h), $V_o = \frac{1}{100}$ of the starting fermentation medium (ml), and t=time of fermentation after the start of the feeding phase (hours). The plasmid can be pET29aUKM5, as described herein.

In some embodiments, the method can further include preparing a two-chain pro-UK mutant, e.g., two-chained M5 (tcM5), by passing the pro-UK mutant over plasmin bound to a substrate, e.g., an agarose-based gel filtration matrix such as Sepharose®.

In other aspects, the invention includes purified pro-UK mutant polypeptides, such as flexible loop mutants, e.g., M5 (both as described herein), e.g., produced according to the methods described herein. The isolated pro-UK mutant polypeptides have a purity of 95% or greater, i.e., they are in compositions in which at least 95, 96, 97, 98, or even 99% of the protein in the composition is the pro-UK mutant polypeptide. The invention also features compositions including pro-UK mutants, e.g., made according to the new methods, and an excipient, e.g., an acidic excipient (such as acetic acid, e.g., at a pH of 5.4), as well as compositions including an aliquot (e.g., of 20–40 mg) of a pro-UK mutant, e.g., made according to any the new methods, packaged with directions for use in administering as a bolus or by infusion to a patient exhibiting symptoms of a stroke or a heart attack.

In another aspect, the invention also includes a purified culture of E. coli type B strain bacteria BL21/DE3 RIL, wherein bacteria in the culture contain an expression plasmid encoding a pro-urokinase flexible loop mutant polypeptide, such as plasmid pET29aUKM5.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF THE DRAWINGS

FIGS. 2A to 2F are graphs representing in vitro lysis of $^{125}$I-labeled plasma clots (0.2 mL) in a plasma milieu (4 mL) by M5 (3.0–14.0 µg/mL) (FIGS. 2D–F) or pro-UK (0.5–3.0 µg/mL)(FIGS. 2A–C) over a fibrin-specific (<25% fibrinogen degradation) dose range. The maximal rate of lysis, as reflected by the steepest slope, was about 70–100%/hour for M5 and 40–50%/hour for pro-UK. FIGS. 2B and 2E show plasminogen remaining (versus concentration of M5 or pro-UK), and FIGS. 2C and 2F show fibrinogen remaining (v. concentration of M5 of pro-UK), which indicate whether lysis was fibrin-specific or non-specific. The experiment consists of incubating both pro-UK and M5 in human plasma for 5 hours (37° C.) and then measuring the remaining plasminogen and fibrinogen. Their consumption is a measure of conversion to the two-chain enzyme, i.e., a measure of stability.

DETAILED DESCRIPTION

Figure 1A:
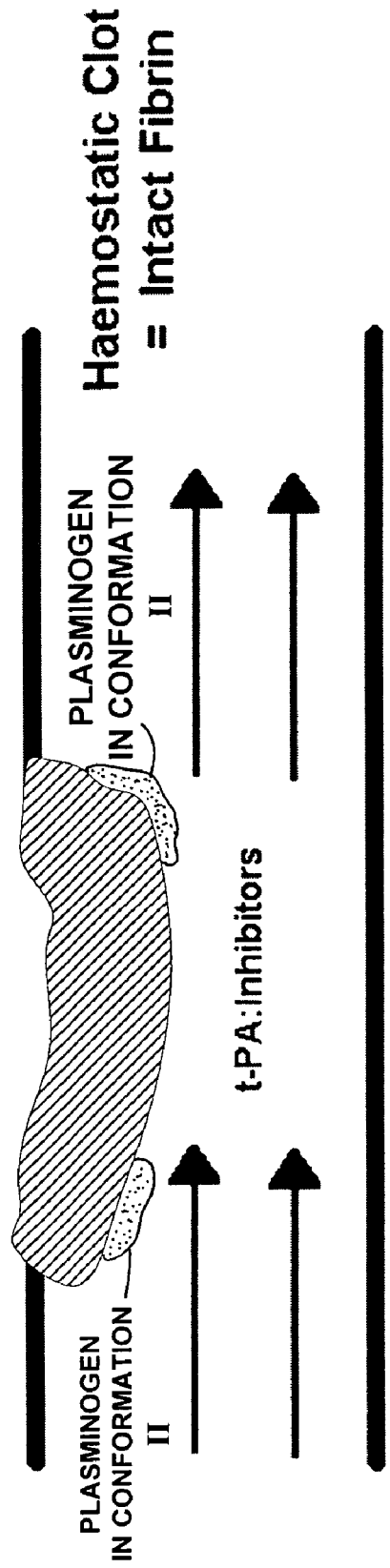
FIGS. 1A and 1B are schematic diagrams illustrating a "good," wound sealing fibrin clot (1A) and an occlusive "bad" thrombus in blood vessels (1B).

Certain mutant forms of pro-UK, so-called "pro-UK mutants," once activated, have a catalytic efficiency that is higher than UK. In a plasma milieu in vitro or in vivo they can induce clot lysis that is twice as rapid as pro-UK (or t-PA). The rate is sufficiently rapid to also make the pro-UK mutants more efficient, e.g., the total amount of pro-UK mutant needed is less than what is needed when using pro-UK or t-PA. At the same time, the wound sealing, hemostatic fibrin "good" clots are spared. The bad clots are occlusive thrombi or emboli that include partially degraded fibrin. The pro-UK mutants are selectively targeted to the plasminogen bound to these occlusive clots. On the other hand, the good clots are comprised of intact fibrin, and the pro-UK mutants are relatively inactive against plasminogen bound to these good clots.

Our theory to explain how the pro-UK mutants can preferentially lyse the occlusive clots and spare the wound sealing clots is based on the realization of the importance of the fact that their substrate, plasminogen (whose activation converts it to plasmin, which lyses the fibrin in the clots), takes on three different conformations. In its first conformation, also known as the "closed" conformation, plasminogen is unbound and this is the form in which it is present in the blood.

UK, the activated form of native pro-UK, activates plasminogen in this first conformation, and thus causes non-specific hemorrhagic diathesis, i.e., a hemophilia-like state. Because pro-UK at therapeutic doses is unstable, it is readily converted to UK, and thus causes this hemophilia-like problem, just as when UK is administered directly. The pro-UK mutants are designed to be much more stable than native pro-UK, and are thus not converted to UK as readily, even at therapeutic doses. As a result, they do not activate plasminogen in this first conformation. They therefore remain inactive.

Although it has been said that plasminogen has only one fibrin-bound, or "open" conformation, we have realized the importance here of the facts that plasminogen actually has two different and distinct conformations on fibrin and that these provide the basis for distinguishing "good" from "bad" fibrin. One conformation takes place when plasminogen is bound to an internal lysine on fibrin fragment D, which is present on intact fibrin. The other is when it is bound to the carboxy-terminal lysines on fibrin fragment E. This binding site is exposed only after some fibrin degradation, and plasminogen bound to this site is known to be highly preferentially activated by pro-UK, and, therefore, mutant pro-UK. By contrast, t-PA preferentially activates the plasminogen on fibrin fragment D (intact, undegraded fibrin).

This difference provides an explanation for why mutant pro-UK spares hemostatic or "good" fibrin for the following reasons. When hemostatic fibrin forms to seal an injury, it acts like a bandage and causes no interference with blood flow. It remains intact and, by definition, has only the plasminogen binding site of fragment D. Pro-UK mutants, because of their superior stability (they remain in the pro-enzyme form), have little activity against this plasminogen.

By contrast, when an intravascular clot forms, it impedes or arrests blood flow, which triggers the local release of t-PA stored in the vessel wall, and some fibrin degradation occurs. This exposes the new plasminogen binding sites on fibrin fragment E. Plasminogen bound to these sites is especially (~200–300 fold more) sensitive to activation by mutant pro-UK (zymogen pro-UK) compared to plasminogen bound to fibrin fragment D. Due to the superior stability of the pro-UK mutants, they are able to exploit this important difference between "good" and "bad" fibrin clots at therapeutic concentrations, and thereby can induce effective clot lysis without degrading a hemostatic plug, which seals an injury.

As illustrated in FIG. 1A, when plasminogen contacts and binds to intact fibrin in a blood clot, it takes on a second conformation compared to plasminogen in circulating blood. Intact fibrin is found in newly forming, wound sealing clots (and plasminogen binds to internal lysines of fibrin). In this conformation, plasminogen is susceptible to activation by t-PA, but not pro-UK mutants, which we have found spare clots that contain plasminogen in this second conformation. T-PA is not normally present in the blood stream (only bound by t-PA inhibitors, as shown in FIG. 1A), so although plasminogen binds to fibrin in newly forming, wound sealing clots, there is no unbound t-PA to activate the plasminogen, and so it does not lyse the fibrin. However, as soon as the blood clot grows too large or dislodges and moves to a narrower vessel, and the clot occludes the vessel, t-PA is secreted from the walls of the occluded blood vessel and starts activating the plasminogen in its second conformation. The activated plasminogen is converted to plasmin, which in turn starts lysing and degrading the fibrin in the clot.

Figure 1B:
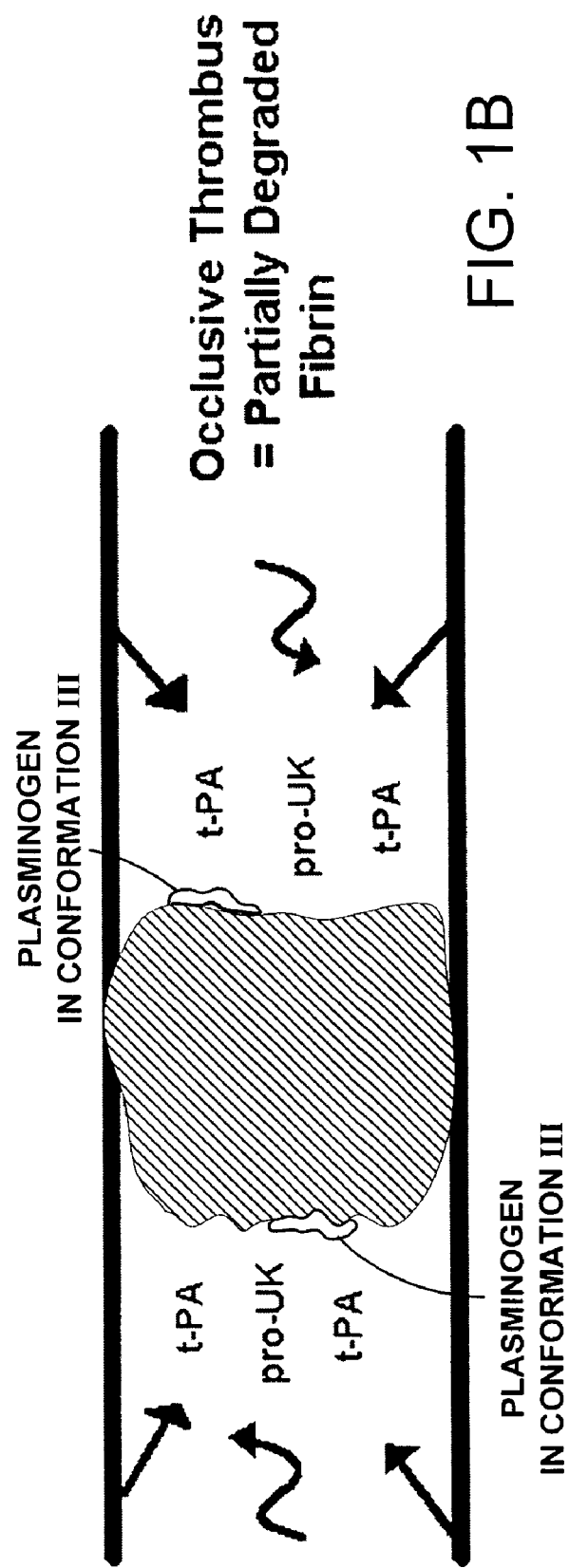

As illustrated in FIG. 1B, the degraded fibrin in occlusive blood clots induces the plasminogen to take on yet a third conformation, because it is now binding to additional binding sites (lysine residues on carboxy terminus of fibrin that are presented only in degraded clots) on the degraded fibrin that are not available in intact fibrin. It is plasminogen in this third conformation that the pro-UK mutants preferentially activate, while sparing plasminogen in its second (and first) conformations. Thus, the pro-UK mutants preferentially cause the lysis of occlusive, bad clots, and do not generally cause the lysis of newly forming, wound sealing, good clots.

We have also learned that pro-UK mutants, once activated into their two-chain form, are significantly more rapidly and efficiently inhibited than UK (the active form of pro-UK) by a plasma inhibitor called C1-Inactivator, which has relatively little effect on UK. The C1-Inactivator is a substrate for two-chain pro-UK mutants, and prevents them from binding to their natural substrate, plasminogen. The more efficiently the two-chain pro-UK is neutralized in the blood, the less non-specific effects there will be, and the more the enzymatic activity will be confined to the immediate vicinity of an occlusive blood clot. These differences represent additional evidence that the catalytic site of two-chain pro-UK mutants is not identical to that of UK.

Pro-UK Mutants

Native pro-UK is a protein having 411 amino acids, with several different domains including the so-called "flexible loop" at amino acid locations 297–313. The pro-UK mutants useful in the new methods, devices, and compositions described herein include those that increase the stability of pro-UK, that can be administered at therapeutic doses, and that preferentially activate plasminogen in its third conformation on degraded fibrin found in occlusive blood clots, and spares wound sealing clots that comprise mostly or entirely intact fibrin. Thus, useful pro-UK mutants include those described in U.S. Pat. No. 5,472,692 (incorporated herein by reference in its entirety), such as the pro-UK "flexible loop" mutants, which are those in which one of several amino acids in the flexible loop of the pro-UK protein (e.g., $Gly^{299}$, $Lys^{300}$, or $Glu^{301}$) is replaced by a neutral amino acid such as alanine (Ala) or an amino acid that can take on only a weak positive charge, such as histidine (His). Specific examples include $Gly^{299} \rightarrow Ala$, $Lys^{300} \rightarrow His$ (referred to herein as the "M5" pro-UK mutant), $Lys^{300} \rightarrow Ala$, or $Glu^{301} \rightarrow His$ mutants.

The pro-UK mutants are much more stable in blood than native pro-UK, because they do not induce the formation of plasmin, and thus should be at least two, three, or four times as stable in blood than native pro-UK. The pro-UK mutants also have a lower intrinsic activity than native pro-UK, and once activated into their two-chain form, the pro-UK mutants can, but need not, have a higher level of activity when activating plasminogen. For example, the specific activity of two-chain M5 is about 100,000–200,000 IU/mg, depending on conditions and methods of measuring, which vary from the same to double the catalytic activity of native UK.

As will be described in detail below, these pro-UK mutants are shown to have significant advantages over pro-UK and other thrombolytic agents, and these advantages allow them to be used in a variety of new methods and devices useful for thrombolysis and treating various cardiovascular disorders in situations where administration of thrombolytics currently has been too risky or even contraindicated, e.g., after an apparent stroke or heart attack, or in the post-operative period, a time when the incidence of thromboembolism is particularly high.

Pro-UK Mutants Dissolve Occlusive Clots more Effectively than Pro-UK and Spare Wound Sealing Clots One of the pro-UK flexible loop mutants, M5, has been tested in vitro and in vivo in two animal species, and shown to dissolve clots twice as fast and more efficiently (i.e., the total amount of M5 needed to achieve lysis of 50% of the lung clots in a dog was half that of pro-UK) than pro-UK. The mutant was also far more stable in blood than native pro-UK. Of significant importance was the fact that hemorrhagic side effects normally associated with thrombolytic agents was not seen with this pro-UK flexible loop mutant. These findings have been published in Liu et al., Circulation Research, 90:757–763 (Apr. 19, 2002).

In the field of thrombolysis, the "Holy Grail" has been defined as thrombolysis without bleeding, i.e., without associated interference with hemostasis. These two seemingly contradictory effects have never been achieved before with one drug. Based on the findings described herein, it is now clear that pro-UK mutants, e.g., the pro-UK flexible loop mutants such as M5, can achieve this goal, and due to their exceptional catalytic efficiency against plasminogen, can dissolve clots faster than other known thrombolytic agents as well.

The combination of superior safety and efficacy of specific pro-UK mutants has the potential to revolutionize the use of thrombolytics for the treatment of heart attacks, strokes, and other blood clot-related diseases. Furthermore, M5 and other pro-UK mutants, such as the pro-UK flexible loop mutants, are expected to be safe for human administration, because (1) they are essentially a natural human protein (99.8% similar to pro-UK, in general, only 1, 2 or 3 of 411 amino acids are changed compared to pro-UK), (2) they are free of antigenic (immunologic) reactions, and (3) naturally occurring human pro-UK and recombinant human pro-UK from E. coli have already been safely administered to about 5,000 patients in Phase III clinical studies.

New Applications of Pro-UK Mutants

The pro-UK mutants can now be used in new methods as well as in new devices for use in various thrombolytic therapies.

Methods of Lysing Blood Clots

1. Stroke

One of the new applications is the treatment of stroke. A stroke is caused by damage that may be either ischemic, due to a blood clot obstructing flow, or hemorrhagic, due to a broken vessel. About 70% of the time, a stroke is due to a clot and therefore is amenable to treatment by a thrombolytic agent, provided it is given in time. One thrombolytic, t-PA is currently approved for this use. However, it is rarely used in practice because it causes a serious brain hemorrhage in at least 10% of the cases. Since this complication is much more visible in the individual patient than the benefit from the drug, physicians have been reluctant to use this treatment. This high risk of hemorrhage with t-PA is probably related to the property of t-PA, that causes it to target intact, or hemostatic fibrin.

Unfortunately, it is difficult and time consuming to fully diagnose the cause of a stroke, but an accurate diagnosis is critical for treatment with t-PA or other available thrombolytic agents. Administering a thrombolytic agent to a stroke victim who has a blood clot may be, at least theoretically, a proper therapy, but administering the same thrombolytic agent to a stroke victim who has a broken blood vessel in the brain will exacerbate the problem and can kill the patient. Although it takes time to confirm a diagnosis, the basic symptoms of stroke exhibited by a person (such as sudden onset of one-sided paralysis) can be readily determined by one of skill in the medical field, such as an EMT, a nurse, or a doctor, or even a layperson with minimal training.

The new discovery that pro-UK mutants such as M5 spare hemostatic fibrin, makes it possible to treat patients with a possible ischemic stroke safely and remove the stigma and potential danger associated with current thrombolytic agents. Since M5 spares hemostatic fibrin, it will not aggravate hemorrhages in the brain. Thus, it is now possible to safely treat all strokes immediately without delaying treatment by time-consuming diagnostic procedures (e.g., CT scan).

Currently, pro-UK has been in clinical trials for ischemic stroke using a complicated intra-arterial route to infuse the drug directly to the location of the clot. This greatly complicates the treatment, and a ~10% incidence of brain hemorrhage was also found. However, unlike t-PA, which must be administered within three hours after stroke onset, the use of pro-UK was associated with benefit up to 6 hours after stroke onset. By contrast, pro-UK mutants such as the flexible loop mutants (e.g., M5) can be given intravenously, will significantly lower the incidence of hemorrhagic complications, and extend the window of time during which treatment is possible well beyond that possible for t-PA, the only thrombolytic approved for this indication.

The intra-arterial administration of pro-UK mutants will also provide additional efficacy and safety in the treatment of stroke patients. The intravenous dose of M5 is estimated to be 120–200 mg/hour (e.g., 100, 125, 150, or 175 mg/hour), whereas the intra-arterial infusion rate will be 50–100 mg/hour (e.g., 60, 70, 80, or 90/mg/hour).

2. Heart Attack

A heart attack occurs when one of the coronary arteries is blocked, e.g., by a blood clot. The timing of reperfusion after a heart attack is critical, because the longer the heart muscle is without oxygenated blood, the more muscle cells are damaged and die. At present, heart attack victims are typically taken to a hospital, diagnosed, and then treated by a coronary angioplasty, which mechanically opens the blocked coronary artery. However, valuable time (typically 90–120 minutes after the onset of symptoms of a heart attack) is lost transporting the patient to a hospital, substantiating the diagnosis, and setting up the catheterization room and assembling the personnel to perform the angioplasty. This first 1 to 2 hours after a coronary occlusion has been called the "Golden Hour" because it is the time during which the maximum salvage of heart muscle and the maximum reduction in mortality is possible. The basic symptoms of a heart attack exhibited by a person (e.g., a typical type of chest pain associated with some shortness of breath) can be readily determined by one of skill in the medical field, such as an EMT, a nurse, or a doctor, or even a layperson with minimal training.

Unfortunately, t-PA and other thrombolytic agents are not used during this time because they are known to be inimical to the angioplasty procedure (they increase both the bleeding and the clotting complications), which is the current standard treatment.

Based on the newly discovered property of the pro-UK mutants that they remain stable and inert in blood and also do not lyse hemostatic, wound sealing clots, these pro-UK mutants can be safely administered to potential heart attack victims immediately after the emergency medical technicians ("EMTs") arrive on the scene. No confirmation of the diagnosis would be required, and thus patients can be treated even on a mere suspicion of a heart attack. Thus, the pro-UK mutants such as M5 are ideally suited for use in ambulances, and can be used to fully exploit the therapeutic potential during the "Golden Hour." Furthermore, by the time the patient arrives at the hospital, the occlusive blood clot may have been dissolved by the thrombolytic therapy started in the ambulance, avoiding the immediate need for an invasive angioplasty.

The pro-UK mutants can also be administered preceding percutaneous transluminal coronary angioplasty ("PTCA") or similar invasive vascular procedure, to improve the benefits of PTCA by lysing the fibrin clot component of the lesion, while simultaneously avoiding bleeding complications that could arise should the blood vessels be damaged during the procedure. It has been shown that the results of PTCA are better when the clot that is associated with the atherosclerotic plaque is removed, and thus the pro-UK mutants are especially well suited to this adjunctive therapy.

For treating a suspected heart attack, the pro-UK mutants are administered by intravenous infusion at a rate of 120–200 mg/hour, e.g., 140, 160, or 180 mg/hour.

3. Pre- and Post-Operative Thrombolysis

In general, thrombolytic agents are strictly contraindicated prior to and for at least 2–3 weeks after surgical procedures, because these agents cause the lysis of hemostatic fibrin that seals the surgical wounds. At the same time, the post-operative period is a high risk period for venous thromboembolism (lung clots) and also for heart attack. Unfortunately, because of the bleeding complications, thrombolytic treatment with currently available agents has not been available for these patients.

The new methods include the administration of pro-UK mutants just prior to and/or after surgical procedures to treat these thrombotic complications of surgery with little fear of causing systemic bleeding or preventing the formation of beneficial hemostatic blood clots that seal the surgical wound. For these methods, the pro-UK mutants are administered by intravenous infusion at 120–200 mg/hour, e.g., 140, 160, or 180 mg/hour.

For example, the pro-UK mutants can be administered after operations known to be associated with a high risk of embolisms, such as hip replacement surgery, and other massively invasive procedures.

4. Clearing Lumens of Catheters and other Devices of Blood Clots

Because mutant UKs (i.e., activated, two-chain pro-UK (tcpro-UK) mutants) are now known to have such a high efficacy and rate of dissolving blood clots compared to other known thrombolytic agents, such as t-PA, they can be used to clear lumens within catheters, syringes, pumps, artificial kidney machines, heart-lung machines, and other blood transporting devices of blood clots.

Low molecular weight (LMW) mutant UK comprising essentially the catalytic domain of the complete mutant UK molecule, e.g., tcpro-UK flexible loop mutants such as tcM5, can be used in a way similar to the way low molecular weight UK is used in the field. Its smaller size (33K vs. 50K) improves diffusion, which has advantages under certain circumstances. LMW mutant UK can be obtained by cleaving mutant UK at the $Lys^{135}$ amino acid location of the molecule, e.g., with plasmin, e.g., using Sepharose®-bound plasmin. The LMW mutant UK has the same catalytic activity as full-length mutant UK, but due to its lower molecular weight it diffuses better, which is advantageous for this particular use.

Devices that Lyse Blood Clots

1. Intravascular Balloons

The provision of a coating of the two-chain activated form of a pro-UK mutant (tcpro-UK mutant) such as tcM5, on angioplasty balloons has significant utility. The uniquely high activity of mutant UK makes it especially good for balloon angioplasty to dissolve the clot that is commonly present, the removal of which improves the results of angioplasty and reduces the risk of re-occlusion.

In other embodiments, mutant UK can be delivered directly to an angioplasty site, e.g., by being incorporated on or in a coating on angioplasty balloon catheters and other invasive vascular devices and implants. Such coating may be both for anti-thrombogenic purposes and to attack and dissolve pre-existing clots.

Direct delivery of the rapidly reactive mutant UK to an occluded vascular site combined with an invasive vascular procedure to remove clot or reform plaque or other stenotic structures provides significantly improved results. In particular, a combined or consecutive local administration of mutant UK and balloon angioplasty provides a highly effective cooperative action.

The combination has practical advantages. While it is effective to employ the same balloon for both drug delivery and vessel expansion, direct delivery of mutant UK to an occlusion in other ways is seen also to lead to useful benefit. For instance, mutant UK can be delivered by a drug-delivery guide wire during its placement, or on a placement tube during its introduction, as a step preceding moving the balloon to the site. In another case, a mutant UK delivery probe may be deployed over a guide wire or through a placement tube before insertion of the balloon catheter. In cases involving little or no delay between introduction of a fibrinolytic agent and balloon angioplasty, a distal, non-inflatable end portion of a balloon catheter can be constructed with a delivery layer such as described below. Such end portion is thrust against an occluding clot as the distal end of the catheter shaft arrives and wedges into a stenotic region. The squeezing pressure of this forward thrust can deliver the suspension of mutant UK to an occluding clot or other stenotic region, e.g., a site for stent placement. In other cases, special purpose mutant UK delivery balloons, located either distally or proximally of the angioplasty, dilatation, or stent-placement balloon on the balloon catheter shaft may be utilized.

Figure 7:
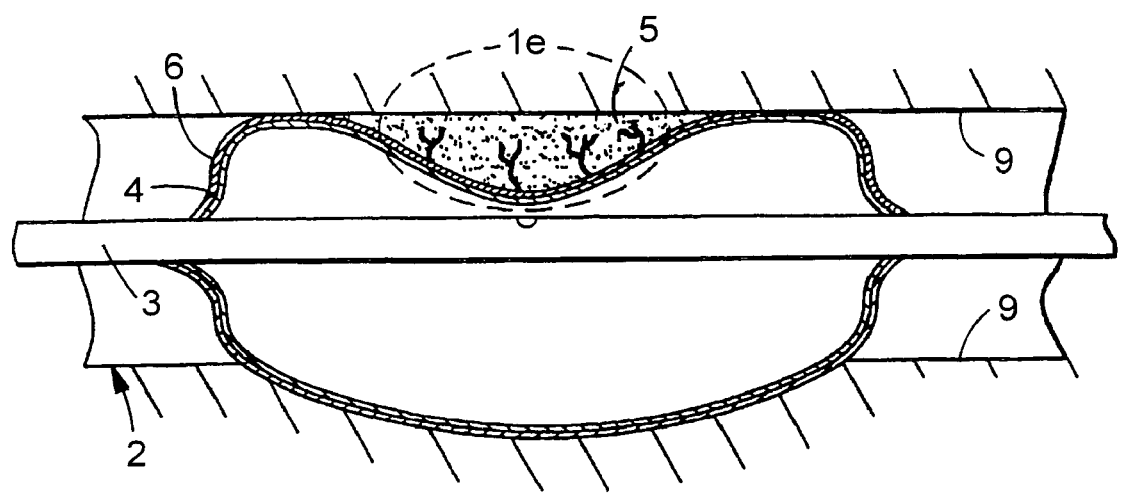
FIG. 7 is a schematic of an expandable intravascular balloon with a coating that contains an activated two-chain pro-UK mutant ("mutant UK"), such as two-chain pro-UK mutant M5 ("tcM5").

In one implementation (shown in FIG. 7), the angioplasty, dilatation, or stent-placement balloon 4 itself forms a part of the direct drug delivery system. The balloon catheter can be made of any conventional form, e.g., suited for insertion by any percutaneous or cut down procedure. It is constructed typically to be introduced over a guide wire and/or a placement tube or catheter 3. The exterior of the balloon is provided with a carrier layer 6, such as a swellable polymer hydrogel coating, containing a suspension of mutant UK, which is released by application of pressure upon the carrier layer 6 by expansion of the balloon 4 against the walls 9 of the stenotic or occluded region 1e. As shown in FIG. 7, the balloon 4 is expanded against plaque 5 on vessel wall 9.

In certain implementations, the carrier is compressible or sponge-like, while in others the layer may be less compressible or incompressible, with open pores that upon application of pressure on a clot or stenotic region forces portions of the clot to enter the pores and contact the mutant-UK agent.

In some embodiments, the carrier uniformly surrounds the balloon, and in other embodiments it is an attached layer or membrane.

We note that many balloons for angioplasty are formed of inextensible material, such as bi-axially oriented polyester tubing. The surface of such material may be metallized, as with tantalum, to form tantalum dioxide when exposed to oxidizing conditions, following which a thin layer of nitrocellulose may be applied, capable of carrying proteins such as provided here. The thickness of the coating may be one or a few thousandths of an inch in thickness, to tightly conform to the balloon. Even in such small thickness, it may be rendered porous, in the known way of evaporation techniques of the first of two solvents from a slurry of nitrocellulose. The porosity provided in this manner enhances the carrying capacity of the film for the suspended enzyme.

Direct administration of the mutant UK by such means as described in conjunction with the reformation of angioplasty or dilatation, has many anticipated advantages: lysis of clot; reduction of stenosis; clearing of clot from plaque thereby lowering the risk of clot regrowth and restenosis; and to provide an improved plaque bed for seating a contemporaneously or subsequently placed stent. All of this is foreseen to occur with little deleterious effect. Blood inhibitors of mutant UK and plasmin (such as the C1 Inhibitor) will ensure that the fibrinolytic effect remains local, thereby eliminating bleeding risk.

In regard to details of construction, the drug delivery device of any form is constructed to protect the mutant UK from substantial reaction with blood constituents during introduction, prior to balloon inflation. In the case of a drug delivery guide wire or placement tube, the drug may be contained within a lumen of the guide wire or tube and then delivered in a radial or axial jet in a selected or in all directions by activation of a plunger via a flexible push wire that extends the length of the guide wire to the operator. Other pumping or displacement actions described in the literature may likewise be employed. In the case of an independent drug delivery device operating over a guide wire, it too may house the drug during transit, and protect it from interaction with blood. Its larger size enables more complex jetting arrangements. These may be used in conjunction with expansible members or a balloon that may spread apart the clot and plaque to enable better application of the agent, but without the expansion force associated with true angioplasty.

In the case of balloon delivery of mutant UK, carrier-pore retention and compressible micro-chamber arrangements are presently favored to carry and protect the mutant UK during transit to the site.

In one arrangement, a thin hydrophilic layer is provided over the exterior surface of an angioplasty balloon. It is formed for instance of nitrocellulose by the known film-form dipping of the balloon, followed by differential solvent leaching to leave an open, porous structure. The layer is constructed to carry the suspension of mutant UK in the depth of its pores, in a position relatively protected from blood, and sufficiently bound to the porous structure to avoid excessive loss during insertion movements. The layer is constructed to be pressure-sensitive for release of the agent with application of modest balloon pressure. By preliminary inflation of the angioplasty balloon against the stenotic walls, the suspension of mutant UK may be expressed from the pores and applied to the clot and/or plaque. To prevent escape of the suspension at the ends of the elongated balloon, circumferential end bands of solid coating, not porous, are provided to block end-wise flow. Thus, the mutant UK suspension flows outwardly to the surrounding target. The thickness of the porous delivery layer may be 0.5 millimeter (0.020 inch) or more or less, the selection of thickness being related to the size of the balloon (thicker layers more tolerable in larger balloons), the quantity of drug to be delivered, and its level of dilution. For example 0.1 mg/ml can provide a total dose of 0.05–0.1 mg. In other examples, the porous layer is formed of porous polystyrene or other biocompatible drug carrying materials. In another case, the delivery layer is an open cell hydrophilic foam adhered to the exterior wall of the balloon. In all such cases a lubricious surface (e.g., of hydrophilic polymers-or polytetrafluoroethylene) may be provided to aid transit during the sliding movements of insertion.

In another arrangement, a set of micro-chambers formed by highly flexible plastic film, capable of being filled with the mutant UK suspension, are secured about the exterior surface of the balloon. For instance, the micro chambers may be of parallel tubular form in longitudinal or circumferential array. The chamber walls are relatively weak, as at scored lines, adapted to rupture under selected pressure to release the mutant-UK suspension in a well-dispersed pattern. In this form, a lubricious coating may be thoroughly applied to the exterior of the balloon for ease of insertion.

In another arrangement, a highly perforated membrane is adhered at a set of closely spaced continuous parallel lines about the balloon, to form elongated flute-like micro-chambers. The membrane has a low, but mutant atmospheric break-through pressure. At atmospheric pressure, and during transit through the vascular system, the walls inwardly contain and protect the suspension by surface tension at the pores. However, under pressurized expansion of the balloon against the vascular wall, the pores of the membrane enlarge. Break-through pressure is exceeded, enabling radial flow of the suspension through the pores of the walls as the chambers are compressed under pressure. Such a perforated film may be provided as a thin-walled exterior electrometric balloon, fitted about a conventional, preformed non-elastic polymer balloon, e.g., made of polyethylene terephthalate (PET). The micropores in the membrane may be produced by a perforating laser or electron beam, or, during formation of the membrane by inclusion of porsigens in a fluid polymer composition of which the membrane is formed. By the sets of flute-form or tubular chambers, or other dividers, uniform dispersion of the mutant UK or M5 suspension around the balloon is provided.

It is feasible to pre-load catheters with the drug in lyophilized form, and store the assembly under suitable drug-storage conditions.

In such cases only sterilized saline or similar fluid carrier need be introduced to create the deliverable suspension prior to use. In other cases, here and with other interventional devices or implants, lyophilized mutant-UK is carried on the surface, and blood in the vessel, e.g., at the site, is relied upon for delivery of the fibrinolytic agent.

However, in presently preferred cases, the mutant UK is packaged separately as a drug in unit dose and applied to the delivery system by the attending scrub nurse or catheter technician. It is stored as a lyophilized preparation not requiring refrigeration, and prepared in suspension, e.g., by the pharmacy. In this case, the attendant applies the drug suspension to the hydrophilic sponge layer or other carrier by an applicator syringe squeegee, which may be an integrated part of the drug package. By rotating a balloon catheter by hand, during applicator strokes, uniform coverage of the surface of a balloon can be obtained. In another case, a close-fitting mold-like container or elastic sleeve is provided into which the balloon end of the catheter is placed and the suspension is poured or applied by a needle syringe about the inserted balloon. The balloon is slightly inflated, and the balloon pushed and pulled repeatedly within the container or sleeve to uniformly distribute the mutant UK suspension over the delivery layer.

In the fluted or tubular chamber versions previously described, the attendant inserts the needle of a syringe to fill each chamber, or the chambers are interconnected so that only one needle insertion is required. An advantage in forming the chambers of porous membrane is that displaced air readily escapes directly through the walls. If the chambers are formed by impermeable film, a permeable air release section is provided at the end of the volume remote from its fill point. In all such cases, care is taken to remove all air.

In employing the various arrangements described, or using other known drug delivery systems on balloons, etc., mutant UK, e.g., tcM5, is delivered directly to the clot and plaque before major angioplastic deformation. For application simultaneous with angioplasty, the timing and duration of drug release relative to increasing balloon pressure can be arranged to enable continued delivery of the mutant UK suspension up to the highest pressure phase of balloon and plaque expansion.

In other arrangements, a drug-delivery balloon, such as one of those described, but not constructed for angioplasty, is mounted on a catheter shaft distal of an angioplasty or dilatation balloon. The drug delivery balloon is first positioned at the operative site and inflated sufficiently to apply the mutant UK. The drug delivery balloon is deflated, the catheter advanced to position the angioplasty balloon, and angioplasty is completed using an unmodified angioplasty or dilatation balloon. In other arrangements, the drug delivery balloon is located on a shaft proximally of an angioplasty or dilatation balloon. The latter is first advanced past the operative site to position the drug-delivery balloon, mutant UK is delivered, the drug delivery balloon deflated, and the angioplasty catheter is withdrawn to position an unmodified angioplasty or dilatation balloon at the operative site, and the balloon angioplasty expansion procedure completed. In another arrangement, the drug delivery system is either provided on the balloon, or distally or proximally as a separate balloon, in one of the manners described herein, while a stent is carried in another location on the same catheter, in ways that are known, so that combined mutant UK direct delivery, angioplasty or dilatation, and stent placement can occur with only one catheter insertion. In some cases, the sequence may be performed in any order, or drug delivery may be performed repeatedly in any order.

In one advantageous case, mutant UK is delivered before or simultaneously with balloon angioplasty, stent placement is performed, e.g., by a self-expanding stent such as formed of mutant-elastic metal, and following placement of the stent, the agents either mutant UK (e.g., tcM5), for immediate action, non-activated, single-chain M5 for adherence and prolonged action, or a mixture, are applied to the interior of the stent after placement. For this purpose, advantageously, the stent is provided with a receptive, or in other cases an enzyme receptive and retentive surface, so that post placement application of M5 to the stent results in retention of M5 at the stent for combating clot formation or restenosis, or for gradual, eluted delivery to the vascular system.

Other delivery interventional and implant placement techniques may likewise be employed in combination with mutant UK (e.g., tcM5) and non-activated M5. Reference is made for instance to U.S. Pat. Nos. 6,409,716 and 6,364,893.

2. Stents and other Implants

The stability of the pro-UK flexible loop mutants, such as M5, make them especially attractive for use on the surface of stents, since they are stable and inert in blood, thus allowing them to be slowly released in a sustained fashion from coatings on stents after implantation. Because the pro-UK mutants are inert until they contact a blood clot, they will have no undesirable side effects if no clots are present, but will be immediately and locally activated, and thus effective in the vicinity of the stent if a blood clot should begin to form on or near the stent. This will prevent re-occlusion and diminish the need of using costly adjunctive therapy with anti-thrombotic agents, such as the IIb and/or IIIa inhibitors, which also carry a risk of hemorrhage and thrombocytopenia.

Figure 8:
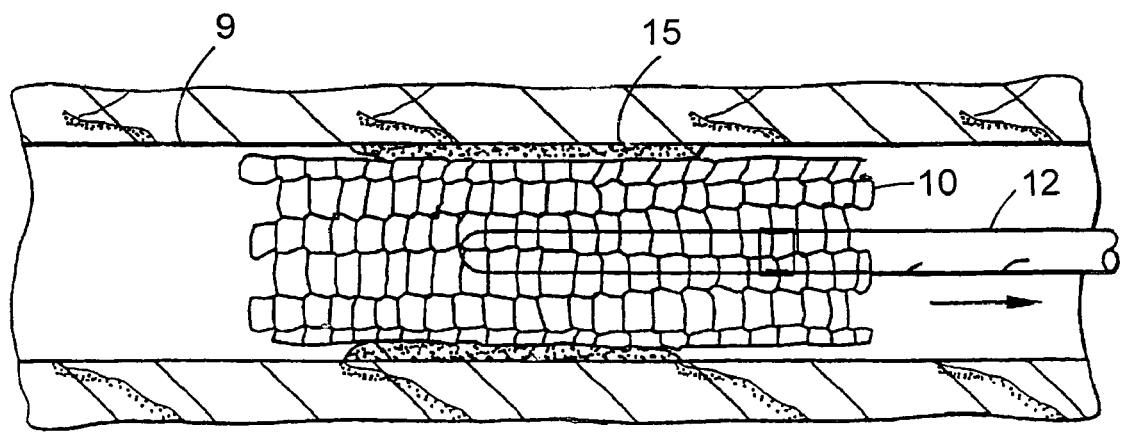
FIG. 8 is a schematic of an implantable intravascular stent with a coating that slowly releases a pro-UK mutant in a controlled, sustained release.

FIG. 8 illustrates a stent 10 and a placement balloon catheter 12 after the balloon catheter has been deflated and is being pulled out of the stent. The stent is compressing the occlusion 15 on blood vessel wall 9. Each wire or plastic fiber of the stent can be coated with a carrier layer that contains a pro-UK mutant, or the stent can be "lined" with a coating layer that is transported by an expandable balloon catheter and then left behind with the stent when the balloon is withdrawn, e.g., as described in U.S. Pat. No. 6,364,893.

Following angioplasty or dilatation, placement of a stent to protect against re-occlusion should be facilitated by the prior or contemporaneous application of mutant UK or M5 as described. A drug-eluting stent can be used, carrying a durable dosage of M5, the zymogenic, single-chain precursor of mutant UK. It is anticipated that this will inhibit clot formation during the early, critical phase when risk of re-clotting is the greatest. Release of M5 will prevent the local deposition of fibrin. In the circulation, M5 will be harmless because it is inert in the absence of fibrin.

The pro-UK mutants can be provided in a varying or homogenous distribution across the thickness of the biocompatible coating or layer to act, or be released, over time in the vascular system or in passages carrying blood. Such coatings can be prepared and applied to various devices using standard techniques. These coatings provide a fresh, unactivated pro-UK mutant such as M5 to act upon blood clots in the immediate vicinity of the device. Known inhibitors of activated, two-chain pro-UK mutants, such as C1 Inactivator, strongly inhibit tcM5, and thus provide another mechanism to confine the activated tcpro-UK mutants to the vicinity of the devices (because they inhibit tcM5 elsewhere in the blood).

Substances that can serve as the coating materials for devices will vary depending on the character or function of the device on which the coating is placed and the site of the clot, or regions susceptible to clotting. For instance, the coating material will be different for application on an elastic balloon (e.g., may be elastic or highly yieldable) versus that for application to a relatively stiff catheter shaft (need not have great elongation). For example, hydrogel coating materials that can be used with pro-UK mutants are described in U.S. Pat. Nos. 6,409,716 and 6,364,893.

The stent may take any of a number of conventional forms. In one case, the stent is a so-called "Palmaz" stent, available from Johnson and Johnson. It is formed as a small, expandable cylinder of biocompatible metal, and has suitably positioned slits. It is sized to be inserted on a placement catheter and introduced percutaneously, and via the vascular system, to the position for placement following balloon angioplasty. The slits are sized and configured to enable the cylinder, when internally stretched by inflation of the placement balloon, to form an "expanded" metal apertured cylinder. In its expanded state, it is constructed to provide support to the vessel wall and resist collapse.

In another case, the stent is a network of super-elastic metal wire material, forming an open structure, of size suitable to be inserted through the vascular system in its reduced size state, and adapted, subsequently, e.g., when heated to body temperature, to expand to its enlarged, vessel wall-supporting size.

In such cases, the stent structure is provided, according to the invention, with a section whose surface, or the entire surface of the stent, is covered with a compliant, ablatable, biocompatible, and bio-erodible coating, adapted to remain intact after expansion of the balloon. Through the thickness of this coating is distributed the mutant pro-UK. Over time, as the bio-erodible, coating sluffs away, fresh mutant pro-UK is exposed-and made available to act upon any adjacent clot. In some cases, the coating may be a lubricious hydrophilic coating, such as described in the referenced patents.

Thus, the stents are of a form familiar to the interventional cardiologist, and constructed to be inserted in a conventional manner. The stent may be pre-prepared with the coating loaded with pro-UK mutant, or mutant UK (or a mixture), and maintained under suitable refrigeration. In other cases a pre-cursor coating is applied, and just prior to use, an aqueous suspension of lyophilized mutant is applied as by needle injection at selected locations. In other cases, a curable coating-forming solution is prepared, through which the pro-UK mutant or mutant UK is distributed. Preparatory to the procedure, the coating is applied by an attending technician to the stent surface and allowed to cure, as by exposure to curing agent, air, moisture, or ultraviolet light, depending upon the composition, following which the stent may be introduced.

In addition, given their newly discovered properties, the pro-UK flexible loop mutants can be used in anti-thrombogenic coatings on other devices that are constructed to be used in the vascular system. For example, the pro-UK mutants can be included in hydrogels and other biocompatible coating materials that can be sprayed, painted, dipped, or otherwise applied to these devices. Specific examples of devices suitable for use with such coating include: vena cava filters, by-pass shunts, guidewires, catheters, grafts, sutures, valves, artificial hearts, and implanted drug delivery devices that administer controlled dosages by active pump action or passively by biodegradation. A shunt is a plastic tube, usually connecting a vein with an artery, e.g., to provide access for kidney dialysis. Since plastic is "foreign" to the body, it stimulates the blood to clot. Thus, a coating of the pro-UK mutants, e.g., M5, can dissolve these types of clots as they form. To clear a shunt of existing blood clots, one would use mutant UK, e.g., tcM5.

Implants may be advantageously located where infusion devices have been known to be effective, e.g., subcutaneous portal pump devices connected by catheter to an artery or vein. In many cases, the regions most at risk for forming clots are at the transition from natural tissue to synthetic. The tissue in such regions, until stabilized during healing, is under stress. It is believed, t-PA will emerge from such tissue and initiate the degradation of the clot, by which the fibrinolytic action of the mutants provided is given opportunity to act. Moreover, we note that this application takes advantage of the property of the pro-UK mutants that they are inert and inactive except in the presence of a fibrin clot.

Summary of New Applications

The newly discovered properties of safety and efficacy allow the pro-UK mutants to be used in a variety of new methods and devices, and many of these uses are contraindicated for known thrombolytic agents. Table 1 below summarizes and exemplifies some of these new uses.

TABLE 1

Clinical Implementations of Pro-UK Mutants and Mutant UK Compared to Known Thrombolytic Agents

| Clinical Condition | Current Thrombolytic Agents (SK, t-PA, Reteplase, TNK-t-PA) | M5 (projected) |
|---|---|---|
| 1. Heart Attack | | |
| General | Used in ~50% eligible Pts. & declining | 75–90% |
| Elderly | Not advised | Advised |
| 2. Pre-PTCA | Contraindicated | Indicated |
| With-PTCA | Not used | Indicated for existing clot and antithrombogenisity |
| Post-PTCA | Not used | Indicated due to Antiplatelet effect |
| 3. Stroke | Limited use within 3 hrs onset | Well suited for use within 6 hour onset |
| 4. Pulmonary embolism | Used only for major emboli (<10%) | Most emboli |
| 5. Deep vein thrombosis | Rarely used | Many patients |
| 6. Peripheral arterial occlusions | Intra-arterial t-PA or UK used | Intra-arterial or Intravenous |
| 7. With Angioplasty of peripheral vessels | Not used | Indicated |

Methods of Making Pro-UK Mutants

Because of these unique characteristics and new methods of use, there is a need to produce single-chain pro-UK mutants, e.g., flexible loop mutants such as M5, in high quantities, at a high level of purity sufficient for administration to human patients, and with the proper protein refolding.

As noted above, pro-UK mutants are proteins that are identical to native pro-UK, but for one or more mutations, such as a single point mutation, e.g., at one or more of the amino acids in the flexible loop (amino acid locations 297–313), e.g., at $Lys^{300}$, $Gly^{299}$, or $Glu^{301}$ with a simple, neutral amino acid such as alanine (Ala), glycine (Gly), and valine (Val), or a weakly positively charged amino acid such as histidine (His). Examples of flexible loop mutants include $Lys^{300} \rightarrow His$, $Lys^{300} \rightarrow Ala$, $Gly^{299} \rightarrow His$, and $Glu^{301} \rightarrow Ala$.

The pro-UK mutants must have the following characteristics: they must increase the stability of native pro-UK in plasma or blood by at least 3 times; they must enable administration in therapeutically effective dosages; and they must preferentially activate plasminogen in a third conformation found on degrading fibrin clots (occlusive clots) and spare plasminogen in its second (and first conformations) found on wound sealing clots (and floating freely in the blood). The pro-UK mutants can be flexible loop mutants, such as M5. They can all be made using various standard techniques that can be scaled up for commercial applications.

Site-Directed Mutagenesis

The pro-UK mutants can be made using site-directed mutagenesis, such as oligonucleotide-directed mutagenesis, which allows the specific alteration of an existing DNA sequence, e.g., native pro-UK. The gene encoding native pro-UK is well-characterized and is available, e.g., from Primm (Milano, Italy) or from the ATCC at Accession Nos. DNA 57329 or Bact/phage 57328. The sequence is also available from the NIH computer database Protein Identity Resource under the name UKHU. See, also, U.S. Pat. No. 5,472,692.

In general, oligonucleotide-directed mutagenesis is accomplished by synthesizing an oligonucleotide primer whose sequence contains the mutation of interest, hybridizing the primer to a template containing the native sequence, and extending it, e.g., with T4 DNA polymerase. The resulting product is a heteroduplex molecule containing a mismatch due to the mutation in the oligonucleotide. The mutation is "fixed" upon repair of the mismatch in, e.g., *E. coli* cells. The details of this method are described, e.g., in Ausubel et al. (eds.), Current Protocols in Molecular Biology, Chapter 8.1 (Greene Publishing Associates 1989, Supp. 13). The details of this method are generally routine, and are described in U.S. Pat. No. 5,472,692.

Several variations of in vitro mutagenesis by primer extension that yield mutants with high efficiency have been developed, as described in Smith, Ann. Rev. Genet., 19:423–463 (1986), and various methods can be used to prepare the pro-UK mutants. One example of a simple site-directed mutagenesis protocol applied to a uracil-containing template, which allows rapid and efficient recovery of mutant DNAs, is described in Kunkel, Proc. Natl. Acad. Sci. U.S.A., 82:488–492 (1985), and Kunkel et al., Meth. Enzymol., 154:367–382 (1987).

Once the pro-UK DNA with the desired mutation is obtained, it must be cloned into a suitable expression vector. This vector must then be introduced into a cell line, e.g., bacterial, mammalian, or yeast, to express the pro-UK mutant, which is harvested from the culture medium, or from the yeast cells, and then purified. These techniques are well known to those of ordinary skill in the field of molecular biology and are described in detail, e.g., in Ausubel et al. (eds.), Current Protocols in Molecular Biology, Chapters 9 and 16, supra; and Sambrook, Fritsch, and Maniatis, Molecular Cloning (2d ed.), Chapter 16 (Cold Spring Harbor Laboratory Press, 1989). The advantage of using mammalian cells, such as Chinese Hamster Ovary (CHO) cells, to express the pro-UK mutant proteins is that they will have a mammalian glycosylation pattern that bacterial and other cells cannot provide. In vitro glycoprotein remodeling can also be used to achieve proper glycosylation when using non-mammalian (or low yield mammalian) cell systems.

There are several ways in which the mutant pro-UK gene can be introduced into a mammalian cell line. As noted, one method involves the transfection of a vector into Chinese hamster ovary ("CHO") cells. In this procedure, the mutant pro-UK gene is co-transfected with a selectable marker, becomes stably integrated into host cell chromosomes, and is subsequently amplified. The CHO cell system is useful because it allows the production of large amounts of mutant pro-UK for long periods of time.

Another expression method involves the transfection of the vector including the mutant DNA into a PET-19B *E. coli* expression system (Novagen, Madison, Wis.). For example, after site-directed mutagenesis, the DNA encoding a $Lys^{300}\rightarrow$His mutant can be sequenced to ensure that the mutation had occurred, and then ligated into the NdeI(XhaI cite of PET-19B, and transformed into *E. coli*. The transformed *E. coli* are then cultured and induced to express the pro-UK mutant by addition of the inducer IPTG at log phase.

Once a vector has been introduced into a mammalian cell line, it also may be desirable to increase expression of the desired protein, e.g., the mutant pro-UK, by selecting for increased copy numbers of the transfected DNA within the host chromosome. Co-amplifying transfected DNA results in a 100- to 1000-fold increase in the expression in the protein encoded by the transfected DNA. There are more than 20 selectable and amplifiable genes that have been described in the literature, but the most experience and success has been with methotrexate selection and amplification of transfected dihydrofolate reductase genes. For example, dihydrofolate reductase-deficient CHO cells may be used to obtain high level of expression of mutant pro-UK genes through co-amplification by selection for methotrexate resistance.

After the mutant pro-UK is expressed, e.g., by a mammalian or bacterial cell line, it must be extracted from the culture medium and purified. In the case of yeast cell culture, the yeast cells must first be disrupted, e.g., by mechanical disruption with glass beads to produce a cell extract that contains the mutant pro-UK. Purification of active mutant pro-UK from culture medium or cell extracts generally involves the steps of 1) liquid/liquid phase extraction or an initial filtration step, 2) hydrophobic affinity chromatography, 3) antibody affinity chromatography, and 4) gel filtration chromatography. These steps are well known to those of ordinary skill in the field of molecular biology, and are described in detail in Current Protocols in Molecular Biology, Chapter 10.

Commercial Scale Production

Although general known methods can be used to make the pro-UK mutants, exceptionally high yields and purity can be achieved, e.g., at a commercial scale, using the new methods of production described herein.

The goal in these new methods is to obtain high expression and high yields of properly folded polypeptides from fermentation and purification procedures. These goals are achieved by careful selection of a combination of specific process parameters such as the type of bacterial strain, the particular expression plasmid, the specific promoter sequences, and the type of cell fermentation and protein purification techniques. By properly selecting these variables, recombinant bacteria are able to synthesize large amounts of the pro-UK mutant, e.g., flexible loop mutant, polypeptides, and it is possible to obtain the pro-UK mutants at high levels of purity. By employing these selected procedures, the properly folded pro-UK mutants, such as M5, can be produced at greater than 96, 97, 98, or even 99% of purity (i.e., they are in compositions in which at least 96% or greater of the protein in the composition is the single-chain pro-UK mutant polypeptide).

To isolate the desired recombinant E. coli strains, it is necessary to go through a number of steps including: (1) mutagenizing the human pro-UK cDNA gene to isolate the desired M5 or other mutant gene; (2) inserting the mutated gene in an appropriate expression plasmid; (3) transforming a selected strain of E. coli with the engineered plasmid; (4) fermenting the transformed cells under appropriate conditions; and (5) isolating the pro-UK mutant protein. Each of these steps will be described in detail.

1) Mutagenesis

The human pro-UK cDNA gene can be treated as described below to isolate the desired pro-UK mutant encoding gene. The general methods described in U.S. Pat. Nos. 5,866,358 and 5,472,692 can be applied to prepare the nucleic acid molecule encoding the particular desired pro-UK mutant polypeptide.

For example, the pro-UK mutants can be made using site-directed mutagenesis, such as oligonucleotide-directed mutagenesis, which allows the specific alteration of the existing native pro-UK nucleic acid sequence. The gene encoding native pro-UK is well characterized and is available, e.g., from Primm (Milano, Italy) or from the ATCC at Accession Nos. DNA 57329 or Bact/phage 57328. The sequence is also available from the NIH computer database Protein Identity Resource under the name UKHU. Production of a gene encoding M5 is described in U.S. Pat. No. 5,472,692.

In general, oligonucleotide-directed mutagenesis is accomplished by synthesizing an oligonucleotide primer whose sequence contains the mutation of interest, hybridizing the primer to a template containing the native sequence, and extending it, e.g., with T4 DNA polymerase. The resulting product is a heteroduplex molecule containing a mismatch due to the mutation in the oligonucleotide. The mutation is "fixed" upon repair of the mismatch in, e.g., E. coli cells. The details of this method are described, e.g., in Ausubel et al. (eds.), Current Protocols in Molecular Biology, Chapter 8.1 (Greene Publishing Associates 1989, Supp. 13). The details of this method are routine, and are described in U.S. Pat. No. 5,472,692.

Several variations of in vitro mutagenesis by primer extension that yield mutants with high efficiency have been developed, as described in Smith, Ann. Rev. Genet., 19:423–463 (1986), and various methods can be used to prepare the nucleic acid molecules encoding the pro-UK flexible loop mutants. One example of a simple site-directed mutagenesis protocol applied to a uracil-containing template, which allows rapid and efficient recovery of mutant DNAs, is described in Kunkel, Proc. Natl. Acad. Sci. U.S.A., 82:488–492 (1985), and Kunkel et al., Meth. Enzymol., 154:367–382 (1987).

2) Insertion of Mutant Gene into Expression Vector

Figure 9:
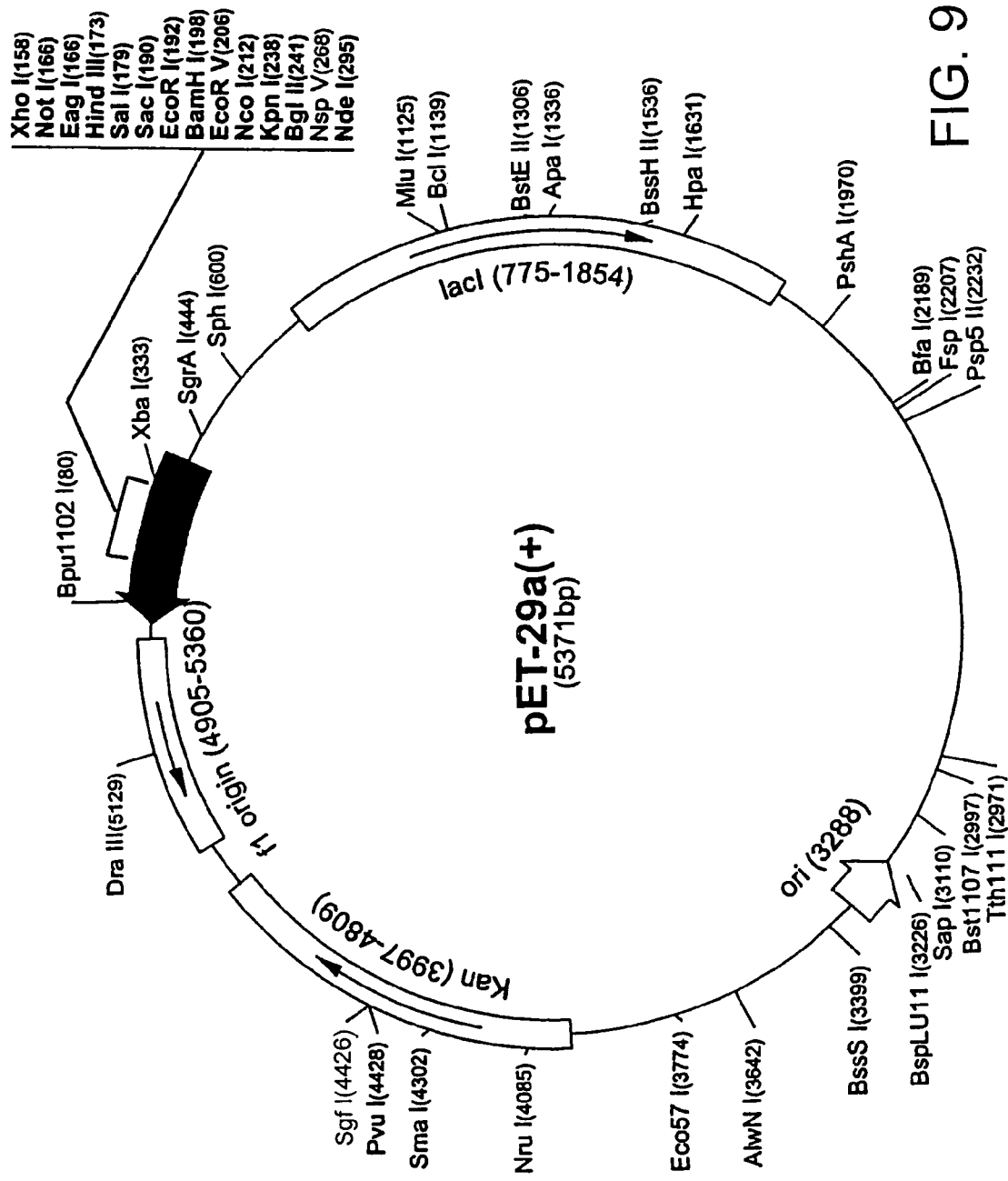
FIG. 9 is a representation of a plasmid (pET-29a) that is used in the new methods of making pro-UK mutants such as M5.

Once the pro-UK DNA with the desired mutation is obtained, it must be cloned into a suitable expression vector. In particular, plasmid pET29a (kanamnycin-resistant), which is shown in FIG. 9 can be used (available form Novagen). For example, pET29aUKM5 (which encodes the M5 pro-UK mutant)(FIG. 10) can be used as the expression vector to produce the specific pro-UK flexible loop mutant M5. In this plasmid, the gene encoding M5 is inserted into the Nde I-Sac I site (see FIG. 10) on the plasmid using standard techniques. The pET-29a plasmid includes specific Phage T7 promoter and Shine-Dalgarno sequences (see, e.g., (Moffatt, B. A. and Studier, F. W. (1986). J. Mol. Biol. 189, 113–130, Rosenberg, A. H., Lade, B. N., Chui, D., Lin, S., Dunn, J. J. and Studier, F. W. (1987) Gene 56, 125–135, Studier, F. W., Rosemberg, A. H., Dunn, J. J. and Dubendorff, J. W. (1990) Meth. Ezymol. 185, 60–89)). The promoter is responsible for the synthesis of messenger RNA while the Shine-Dalgarno sequence should guarantee an efficient translation of the mRNA in the polypeptide chain.

Although this particular plasmid and sequences are known, and the techniques to combine these sequences and plasmids are also well known to those of ordinary skill in the field of molecular biology, the specific combination of these parameters has not been described prior to the present disclosure. The general techniques are described in detail, e.g., in Ausubel et al. (eds.), Current Protocols in Molecular Biology, Chapters 9 and 16, supra; and Sambrook, Fritsch, and Maniatis, Molecular Cloning (2d ed.), Chapter 16 (Cold Spring Harbor Laboratory Press, 1989).

3) Transformation of the Plasmid into a Host Cell

Next, an E. coli type B strain, BL21/DE3 RIL, is used for the expression and production of the pro-UK mutant. For example, insertion of plasmid pET29aUKM5 into E. coli type B strain BL21/DE3 RIL (available, e.g., from STRATAGENE®, USA) induces very high levels of expression of the M5 polypeptide. Interestingly, insertion of the same plasmid into other strains of E. coli (type K-12, type C, or type W, and even other type B strains) does not provide as high a yield of M5.

For example, competent cells of strain BL21/DE3 RIL can be prepared using a calcium chloride procedure of Mandel and Higa (Mol. Biol., 53:154, 1970). A small aliquot, e.g., 200 µl, of a preparation of these cells, e.g., at $1\times10^9$ cells per milliliter, can be transformed with plasmid DNA (approximate concentration from 2 to 10, e.g., 5 µg/ml). Transformants containing the kanamycin resistant plasmids are selected on plates of L-agar containing 30 µg/ml kanamycin.

One or more small colonies are streaked, e.g., with wooden toothpicks, onto L-agar containing the same antibiotic. After incubation at about 34–37° C., e.g., for a time sufficient to establish colonies, e.g., about 8, 10, 12, 15, or more hours, portions of the streaks can be tested for pro-UK mutant production by inoculation into LB medium (containing kanamycin at a concentration of 30 µg/ml) and incubated overnight (e.g., 8, 10, 12, or 15 or more hours), again at about 34–37° C. The following day, the cultures can be diluted, e.g., 1:100, in medium, such as M9 medium, containing the same concentration of kanamycin, and incubated, e.g., for 4, 6, or 8 hours at 34–37° C.

Total cell proteins from aliquots of culture medium ($O.D._{550}$=1 to 1.5) can be analyzed by sodium dodecylsulfate polyacrylamide gel electrophoresis (SDS-PAGE) as described in Laemmli, Nature, 227:680, 1970. A major protein band having a molecular weight corresponding to that of non-glycosylated M5 (45,000 daltons) should be observed for the samples.

Figure 12:
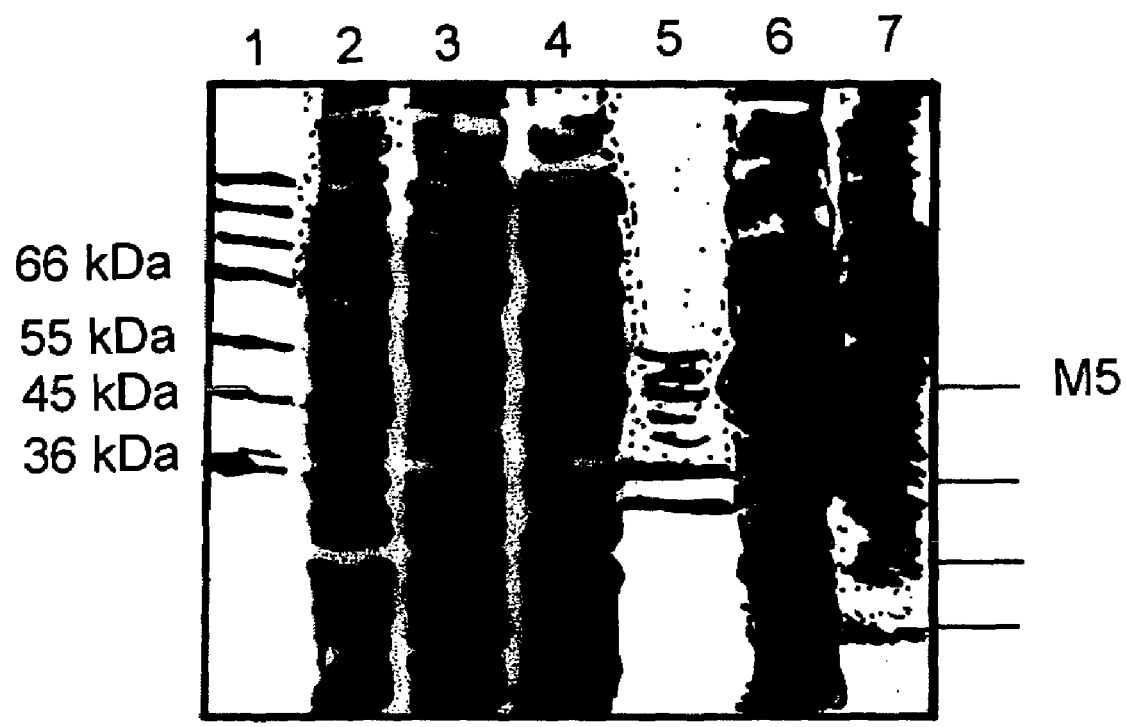
FIG. 12 is a representation of an electrophoresis gel showing the molecular weight of various proteins produced by various strains of E. coli and different plasmids.

FIG. 12 shows typical SDS-PAGE results. Lane 1 includes molecular weight standards. Lane 2 contains BL21 (DE3)RIL[pET29a] supernatant of cells at an OD of 1.5. Lane 3 contains BL21(DE3)RIL[M5-PUK] supernatant of cells at an OD of 1.5. Lane 4 contains BL21(DE3) [M5-PUK] supernatant of cells at an OD of 1.5. Lane 5 contains BL21(DE3)RIL[pET29a] inclusion bodies of cells at an OD of 1.5. Lane 6 contains BL21(DE3)RIL[M5-PUK] inclusion bodies of cells at an OD of 1.5. Lane 7 contains BL21(DE3) [M5-PUK] inclusion bodies of cells at an OD of 1.5. As explained in further detail in Example 13, below, these results indicate that M5 is an insoluble protein, and only the combination of the pET-29aUKM5 plasmid with BL21 (DE3)RIL produced large quantities of M5 (Lane 6).

Using the procedure described above, several additional E. coli host strains were screened with the objective to isolate a transformant strain able to produce M5 at high levels. Plasmid pET29aUKM5 was transformed into the following strains: BL21/DE3, BL21/DE3 pLys, JM109/DE3, and HB 101/DE3. None of these transformed strains was able to yield high quantities of the M5 polypeptide as seen with the host strain BL21/DE3 RIL, indicating that indeed the combination of the specific expression plasmid with strain BL21/DE3 RIL is an important combination to obtain high quantities of M5. The details of these tests are described in Example 14, below.

We note that the use of B strains according to the present invention yields cell extracts with low proteolytic activity, i.e., low contamination with UK.

4) Fermentation of the Host Cells

The transformed bacterial cells must then be cultured at high biomass in appropriate fermentors. The protocol developed and used for the production of pro-UK flexible loop mutants is based on the following two stages of fermentation.

A. First Fermentation Stage (Seed Culture)

The first fermentation phase is carried out in flasks to obtain a seed culture large enough to inoculate the production stage (second fermentation stage). One vial of "working cell bank" (e.g., 0.1 ml–1.0 ml) is diluted in an amount (e.g., 50 to 500 ml, e.g., 100 ml) of sterile medium (e.g., EC-1 medium, details of which are provided in Table 4 in Example 15, below) and growth at about 37° C. overnight with the agitation.

The working cell bank is made of a glycerol suspension of an overnight culture (e.g., LB medium) of the pro-UK flexible loop mutant producing strain (e.g., BL21/DE3 RIL carrying plasmid pET29aUKM5 that encodes M5), and containing an antibiotic to select for bacteria carrying a resistant plasmid (e.g., kanamycin at 30 μg/ml, chloramphenicol at 30 μg/ml, and 0.1% w/v D-Glucose).

B. Second Fermentation Stage

The second stage includes the following steps:

1) the seed culture, prepared in a flask, is added to a fermentor (e.g., a 1:100 dilution in EC-1 medium; e.g., 20 ml into 2.0 liters or 100 ml into 10 liters);

2) the pH in the fermentor is kept at about 6.8 to 7.2, e.g., 7.0, for example, by using a solution of 28% (v/v) ammonia water;

3) dissolved oxygen is maintained at about 35 to 45%, e.g., about 38, 40, or 42%, of air saturation by increasing the agitation speed and by changing the percentage of pure oxygen;

4) the temperature of fermentation is kept at about 34–37° C.; and 5) a nutrient feeding solution that contains one or more sugars (e.g., glucose) and other nutrients (for a specific example, see Table 5 in Example 15, below) is added exponentially when all the glucose initially present is consumed (usually after 8 hours), following the equation $V=V_0 e^{0.18t}$, where V=volume of feeding solution added (ml/h), $V_0=\frac{1}{100}$ of the starting fermentation medium (ml), and t=time of fermentation after the start of the feeding phase (hours).

In this method, gene expression is induced by adding IPTG, e.g., at a final concentration of 1.2 mM, when the fermentation reaches a cell density of about 90 $OD_{600}$.

The post-induction fermentation is generally prolonged for 6 hours to allow the cells to produce the pro-UK mutant. Samples of 0.5 ml are removed from the fermentor every 2 hours for analysis.

5) Isolating and Purifying Pro-UK Mutants

After the mutant pro-UK is expressed by a bacterial cell line, it must be extracted from the cells and purified. Purification of active mutant pro-UK from culture medium or cell extracts generally involves the steps of: 1) pellet recovery, 2) protein refolding, 3) concentration by ultrafiltration, 4) cation exchange chromatography, 5) anion exchange chromatography, 6) hydroxyapatite chromatography, 7) gel filtration chromatography, 8) buffer exchange, and 9) freeze drying. These steps are described in further detail as follows.

1. Pellet recovery

In specific embodiments, the broth from a 2-liter fermentation is collected at about 4° C. at 9950×g for 15 minutes using, e.g., a Beckman J2-MI centrifuge. Other methods can be used to create a pellet. The cellular pellet is resuspended at 4° C. in 1.1 liters of a buffer comprising 0.025 M monobasic sodium phosphate, 0.125 M sodium chloride, pH 7.5 containing 0.1% Triton×100. This slurry is passed through a French-Pressure-Cell 20K (Aminco) at 1000 psi. The temperature is controlled during this operation to about 5–10° C. After each passage through the French pressure cell, the cell suspension is sonicated at 15 mV for about 1 minute, e.g., using a Microson™ Ultrasonic cell disruptor XL (Misonix).

Six passes under these conditions are made to achieve greater than 90% cell breakage (controlled by microscopic observation). A further passage may be made if necessary. Other methods can be used to achieve 90% cell breakage.

The resulting cell lysate is centrifuged at 4° C. at 9950×g for 15 minutes using, for example, a Beckman J2-MI centrifuge. The solid is resuspended in 1 liter of buffer: 0.025 M monobasic sodium phosphate, 0.125 M sodium chloride, pH 7.5 containing 0.1% Triton×100. The slurry is passed again twice through the French press under the conditions described above, and centrifuged at about 4° C. at 9950×g for 15 minutes using the centrifuge.

The slurry resulting from this process is the starting material for the activation and purification process and is divided into suitable aliquots. Other methods can be used to obtain a similar cell lysate slurry.

2. Refolding

In specific embodiments, a quantity of the material coming from the slurry obtained, as described above, corresponding to about 6 g of protein (judged by Lowry or Biuret protein assay) is dissolved in a 1.2 liters of 6 M guanidine HCl, 0.01 M TRIS, pH 8.5, L-cysteine 0.1 M, for at least 10 hours at 4–6° C. The solution is centrifuged at 4° C. at 9950×g for 15 minutes using a centrifuge, and then diluted with 30 liters of a buffer comprising 2.5 M Urea, 0.01 M TRIS, 0.005 M EDTA (pH 8). The solution is stirred gently at 14–16° C. for at least 18 hours. During this period the active product is formed from the previously inactive protein. Other standard methods of protein refolding can be used.

3. Concentration

The solution obtained from the refolding process (2) is pre-filtered, e.g., using an Opticap® 10" cartridge (Millipore), and then concentrated, e.g., about 25 times from its initial volume, using an ultrafiltration system (e.g., a Millipore ProFlux® M12 with Pellicon® 2 cartridges, 10,000 M.W.t. cut off). The concentrated material can then be diafiltrated against two volumes of a buffer consisting of 2.5 M Urea, 0.01 M TRIS, 0.005 M EDTA, and pH 7.6.

4. Cation Exchange Chromatography

The solution obtained from the concentration step (3) is centrifuged at 4° C. at 9950×g for 15 minutes using a Beckman J2-MI centrifuge, and then applied to a cation exchange column, e.g., a HiPrep™ 16/10 SP FF (Amersham Biosciences), previously equilibrated with the same dilution buffer. After loading, the column is washed with two column volumes of the equilibrating buffer followed by four column volumes of 0.01 M TRIS (ph 7.6) buffer. The column is then eluted in fractions with 0.01 M TRIS, 0.5 M sodium chloride, and pH 7.6 buffer.

5. Anion Exchange Chromatography

The pool fractions from cation exchange chromatography are loaded onto an anion exchange column, e.g., a HiPrep 16/10 Q FF (Amersham Biosciences), previously equilibrated with 0.01 M TRIS, 0.5 M sodium chloride, and pH 7.6 buffer. The column flow-through containing the product is collected. After loading, the column is washed using 2–3 column volumes of the equilibrating buffer.

The combined load flow-through and column wash solutions form the input for the next chromatographic column.

6. Hydroxyapatite Chromatography

The material obtained from the anion exchange column is applied to a column of hydroxyapatite, such as a High Resolution (Calbiochem) column, previously equilibrated in 0.01 M TRIS, 0.5 M sodium chloride, and pH 7.6 buffer. After loading, the column is washed with 2 column volumes of the equilibrating buffer, followed by 1 column volume of 1 mM sodium phosphate, 0.5 M sodium chloride, pH 7.6 buffer.

The column is eluted in fractions with 20 mM sodium phosphate, 0.5 M sodium chloride, and pH 7.6 buffer. A pool of these fractions is made on the basis of the quantity and purity judged by the specific activity. Depending on the pool volume, the resulting material may be concentrated by ultrafiltration (e.g., using a Pellicon 2 cartridge, 10,000 M.W.t. cut off) to a suitable volume for the following step.

7. Gel Filtration Chromatography

The material resulting from the hydroxyapatite chromatography is loaded directly (or after concentration) on to a column of HiLoad 26/60 Superdex® 75 (Amersham Biosciences), previously equilibrated in 0.01 M TRIS, 0.5 M sodium chloride, 0.005 M EDTA, pH 8. The column is eluted in fractions using the equilibration buffer.

Pool fractions are selected on the basis of specific activity, SDS PAGE (reduced and non reduced) and HPLC purity.

8. Buffer Exchange

The resulting material, pooled from gel filtration chromatography, is applied to column of HiPrep 26/10 desalting (Amersham Biosciences), previously equilibrated in 0.05 M ammonium bicarbonate buffer. The column is eluted in fractions with this buffer. A pool of fractions is prepared on the basis of OD 280 nm and conductivity.

9. Freeze Drying

The solution resulting from the buffer exchange stage is divided into aliquots, e.g., of 10 mg in vials of 100 ml, and then frozen, e.g., for 2 hours at −80° C. The frozen material is then lyophilized, e.g., using a CT 60e (Heto) freeze-drier for 72 hours.

Alternative methods of protein isolation and purification can be used and are well known to those of ordinary skill in the field of molecular biology. Various protocols are described in Current Protocols in Molecular Biology, Chapter 10.

The new methods described herein can also be used to produce various biologically active fragments of the pro-UK flexible loop mutants. For example, one set of active fragments is known as low molecular weight ("LMW") pro-UK flexible loop mutants. These mutants have the same sequence as the full-length pro-UK mutants, but are cleaved at the $Lys^{135}$ amino acid location of the molecule, e.g., with plasmin or trypsin, to form a smaller size (33K vs. 50K) protein molecule. These LMW pro-UK mutants have improved diffusion characteristics because of their smaller size. These LMW pro-UK mutants can also be activated to produce LMW two-chain mutant UK, e.g., by passing the single-chain form over a column of Sepharose®-bound plasmin. One can also produce full-length, activated pro-UK flexible loop mutants by passing the pro-UK mutants over plasmin bound to Sepharose®, e.g., in columns or in batch methods.

Storing and Administering Pro-UK Mutants

Once the pro-UK mutants are made, they can be lyophilized or stored in physiologically acceptable excipients, such as organic acids, e.g., acetic acid at a pH of about 5.4. The pro-UK mutants are quite stable in such acids, and can actually be stored over time and then administered directly to patients in such an acid solution. The pro-UK mutant proteins can also be combined with other drugs to form compositions that can then be administered to a patient in one solution.

In general, bolus or "loading" doses of the pro-UK mutants will be in the 20–40 mg range. The intravenous infusion dose of pro-UK flexible loop mutants such as M5 is about 120–200 mg/hour (e.g., 100, 125, 150, or 175 mg/hour), whereas the intra-arterial infusion rate will be 50–100 mg/hour (e.g., 60, 70, 80, or 90/mg/hour). Intra-arterial administration of pro-UK mutants will also provide additional efficacy and safety in the treatment of stroke patients.

The pro-UK in lyophilized form can be administered with a device that contains the pro-UK powder in one compartment, and in a second compartment contains a pre-measured amount of an excipient, such as sterile saline, purified water, or some other physiologically acceptable carrier in which the pro-UK powder can be reconstituted. The first and second compartments are connected by a wall such that the wall can be broken by the user of the device just prior to injecting the pro-UK solution. Thus, the device can be stored for long periods of time, and then the pro-UK powder can be reconstituted as required without the need to measure the amount of the excipient.

In addition, the pro-UK can be packaged in specific aliquots and at specific concentrations, e.g., in predetermined dosages ready for administration, along with instructions to administer the pro-UK mutant, such as a flexible loop mutant, e.g., M5, to a person exhibiting symptoms of stroke or symptoms of a heart attack. For example, a plastic IV bag containing M5 for infusion can be labeled for use post-operatively, after angioplasty, or upon observing symptoms of a heart attack or stroke. In addition, a syringe for administering a bolus injection of M5, e.g., for use by an EMT in an ambulance, can be pre-loaded with a bolus of 20, 25, 30, 35, or 40 mg of a pro-UK mutant, such as M5, and labeled for immediate use on a person exhibiting symptoms of an apparent stroke or a heart attack.

EXAMPLES

The invention is further described in the following examples, which do not limit the scope of the invention described in the claims.

The following materials were used in the examples.

Single-chain t-PA was obtained from Genentech (San Francisco, Calif.). UK was prepared by plasmin activation of pro-UK as previously described (Pannell et al., Blood, 69:22–26, 1987), and its concentration was standardized against the UK International reference standard (NIBSC, London, UK). Glu-plasminogen was prepared from DFP-treated human bank plasma. Fragment E-2 was prepared as previously described (Liu et al., J. Clin. Invest., 88:2012–2017, 1991). D-dimer, Soluble fibrin (Desafib), and Lys-plasmin were obtained from American Diagnostica Inc. (Greenwich, Conn.). Fibrinogen (human) and synthetic chromogenic substrate for plasmin (S2251) and UK (S2444) were obtained from Kabi Pharmacia Inc. (Franklin, Ohio). Fibrinogen was radiolabeled with $^{125}$I using Iodogen (Sigma, St. Louis, Mo.). PAI-1 is available from Dupont Merck (Washington, D.C.)

Example 1

Preparation of M5

The gene for native pro-UK has been well characterized (Verde et al., Proc. Nat. Acad. Sci., USA, 81:4727–4731, 1984) and its cDNA was available from Dr. Paolo Sarmientos (Farmitalia, Milano, Italy). The site-directed mutant [Lys$^{300}$→His, M5] of pro-UK was constructed and expressed in E. coli as follows: The cDNA of M5 was obtained by site-directed mutagenesis after subdloning the HindIII-BamHI restriction fragment from pFC16 plasmid containing the full-length cDNA of pro-UK (Orini et al., Eur. J. Biochem., 195:691–697, 1991) into an M13 vector (mp18). The expression plasmid for the mutant was constructed by reinserting the mutated HindIII-BamHI fragment into pFC16 and introduced into an E.coli type-B strain. M5 was purified from sonicated cell lysates by chromatography through S-Sepharose®, pro-UK antibody affinity column and Sephadex® G-25 after refolding by standard methods previously described (Winkler et al., Biochemistry, 25:4041–4045, 1986). Trace amounts of two-chain M5 (tcM5) were removed by passage over benzamidine Sepharose® followed by treatment with DFP as previously described (Liu et al., J. Biol. Chem., 270:8408–8410, 1995). Purified M5 was observed as a single band on reduced SDS-PAGE. Protein concentration was determined from absorbance at 280 nm using the extinction coefficient ($E^{1\%}_{280\ nm}$=1.36) for pro-UK. Plasmin resistant mutations (Ala$^{158}$-proUK and Ala$^{158}$-M5) were also made by an additional site-directed mutagenesis at Lys$^{158}$ (Lys$^{158}$→Ala) in both pro-UK and M5.

Example 2

Enzymology of M5

Assay of Plasmin Sensitivity:

Since the activatability of pro-UK is essential for its fibrinolytic efficacy, this property had to be verified. A range of concentrations of pro-UK or M5 (0–5 μmol/L) was incubated with Lys-plasmin (0.1 nmol/L) in the presence of synthetic substrate (S2444, 1.2 mmol/L) in the assay buffer (0.05 mol/L TrisHCl, 0.10 mol/L NaCl and 0.01% Tween80®, pH 7.4) at room temperature. The same range of concentrations of pro-UK or M5 without plasmin was incubated with S2444 as control. The 0.1 nmol/L plasmin had no direct effect on S2444 hydrolysis. The rate of pro-UK or M5 activation was calculated from the OD increase over time squared at 410 nm on a microtiter plate as previously described (Liu et al., Blood, 1993, 81:980–987). The kinetic constants were derived by Lineweaver-Burk analysis.

Intrinsic Catalytic Activity Assay

For hydrolysis of S2444, pro-UK (1.0 μmol/L) or M5 (10.0 μmol/L) was incubated with a range of concentrations (0–2.4 mmol/L) of S2444 in the assay buffer at room temperature. The reaction rate was measured by the linear OD increase over time at 410 nm. 0.01–5.0 nmol/L of UK International Standards was used for the standard curve of S2444 activity of UK. The kinetic constants were calculated from Lineweaver-Burk plots.

Activities of the Two-Chain (tc) Derivatives of Pro-UK and M5

1) Hydrolysis of S2444:

UK or tcM5 was prepared by plasmin treatment of the single chain precursors as previously described (5). UK or tcM5 (4.0 nmol/L) was incubated with a range of concentrations (0–2.4 mmol/L) of S2444 in the assay buffer at room temperature. The reaction rate was measured and the kinetic constants were calculated as described above.

2) Glu-Plasminogen Activation:

Time-absorbance curves of Glu-plasminogen activation were obtained by measuring the OD increase of the reaction mixture with time at the selected wavelength 410 nm. The reaction mixture contained S2251 (1.5 mmol/L), Glu-plasminogen (1.0–10.0 μmol/L) and UK or tcM5 (0.2 nmol/L). The reactants were made up in the assay buffer, and incubated at room temperature. The reaction rates were calculated from the OD increase over time squared as previously described (19). The kinetic constants were calculated from Lineweaver-Burk plots.

3) Glu-Plasminogen Activation by Pro-UK or M5

Glu-plasminogen (2 μmol/L) was incubated with pro-UK or M5 (0.075 nmol/L) in the presence of 1.5 mmol/L S2251. The reaction rates were compared from the OD increase over time.

The kinetic constants for M5 and pro-UK are shown in Table 4, which shows that the catalytic efficiency of two-chain M5 is about twice that of UK (against the synthetic substrate for UK). We have also found that the specific activity of M5 is about 100 K–200 K IU/mg, which is somewhat higher than UK. Nevertheless, the rate of clot lysis is twice as high, as indicated in the differences in kinetics shown in Table 2

TABLE 2

Kinetics analysis of S2444 amidolysis by pro-UK, single-chain M5, UK & tcM5 and glu-plasminogen activation by UK & tcM5

| | kcat (min-1) | KM (µM) | kcat/KM (min µM)-1 | F |
|---|---|---|---|---|
| S2444 (0.03–2.4 mmol/L) Amidolysis | | | | |
| pro-UK | 0.32 ± 0.15 | 51 ± 9 | 0.00627 | 1 |
| M5 | 0.065 ± 0.030 | 52 ± 12 | 0.00125 | 0.2 |
| UK | 180 ± 130 | 78 ± 15 | 2.31 | 1 |
| tcM5 | 350 ± 110 | 75 ± 18 | 4.67 | 2 |
| Glu-Plasminogen (0.1–20.0 µmol/L) Activation | | | | |
| UK | 18.1 ± 0.6 | 11.4 ± 2.1 | 1.59 | 1 |
| tcM5 | 9.2 ± 1.8 | 3.6 ± 1.5 | 2.56 | 1.6 |

Promotion of Pro-UK or M5 Induced Plasminogen Activation by Co-Factors

Fibrin fragment E selectively and potently promotes Glu-plasminogen activation by the intrinsic activity of pro-UK. Therefore, the promoting effect of fragment E2, prepared as previously described, on M5 was evaluated using plasmin-resistant (Lys$^{158}$) mutants of pro-UK and M5. The OD increase over time in the reaction mixture at 410 nm was measured using standard techniques. The reaction mixture contained 1.5 mmol/L S2251, Glu-plasminogen (2.0 µmol/L), and 1.0 nmol/L Ala$^{158}$-proUK or Ala$^{158}$-M5 with or without 5.0 µmol/L fragment E2, in the assay buffer at room temperature. The effects of other fibrin analogs such as fibrinogen (3 µmol/L), soluble fibrin monomer (SFM, 1 µmol/L), and D-dimer (1 µmol/L), were also tested since they do not promote plasminogen activation by pro-UK. The results are shown in Table 3 below, which shows mean values from one experiment done in triplicate.

TABLE 3

Glu-Plasminogen (2 µmol/L) activation by plasmin resistant Ala$^{158}$-proUK or Ala$^{158}$-M5 (1 nmol/L) in the presence of co-factors Reaction Rate (as $\Delta A_{405} \times 10^6/\text{min}^2$)

| Co-factors | A158-ProUK | A158-M5 |
|---|---|---|
| Buffer Control | 4.40 | 0.90 |
| Fibrinogen (3 µmol/L) | 1.20 | 0.19 |
| SFM (1 µmol/L) | 3.80 | 0.62 |
| Fragment E (1 µmol/L) | 29.1 | 7.90 |
| D-dimer (1 µmol/L) | 4.30 | 1.84 |

Fibrin-fragment E, which selectively promotes plasminogen activation by pro-UK (Liu et al., Biochemistry, 1992, 31:6311–6317), had a similar effect on M5, whereas D-dimer and soluble fibrin or fibrinogen induced little or no promotion. For this study, plasmin-resistant mutants (Lys$^{158}$→Ala) of pro-UK and M5 were used to prevent interference from the elaboration of the two-chain enzymes (Table 3).

Inhibition of UK or tcM5 by PAI-1

UK or tcM5 was incubated with PAI-1 in the assay buffer at equal molar concentrations of enzyme and inhibitor (2.0–8.0 nmol/L). After different times of incubation at 25° C., 80 µL of the UK/PAI-1 or tcM5/PAI-1 reaction mixture was added to 20 µL S2444 (final concentration was 1.2 mmol/L). The amount of uninhibited UK or tcM5 was determined from its initial rate of hydrolysis of S2444 as measured at 410 nm. The concentration of free PAI-1 was then calculated by difference. The second-order rate constants were determined by linear regression of a plot of 1/[E] vs. time (where [E] is the concentration of UK or tcM5 at time [t]) as previously described (Hekman et al., Biochemistry, 27:2911–2918, 1988).

The tcM5 was inhibited by PAI-1 with a $K_i$ of $1.3\pm0.3\times 10^7$ M$^{-1}$sec$^{-1}$, which was comparable to that of UK ($1.7\pm0.4\times10^7$ M$^{-1}$sec$^{-1}$).

Comparative Reactions of the Two TC-UK's with Plasma Protease Inhibitors

The active two-chain derivatives of both M5 (tc-M5) and wild-type pro-UK (tc-u-PA) were generated by incubation at 100 µg/ml with plasmin (1.2 µg/ml) in Hepes buffered saline (pH 7.4 and with 1 mg/ml BSA added) for 60 min at 37° C. These were added respectively to pooled human blood bank plasma at 5 µg/ml and incubated at 37° C. At various time points, aliquots of these incubation mixtures were removed and the reaction stopped by dilution into Laemmli SDS sample buffer. These samples were later subjected to Laemmli SDS PAG electrophoresis. After the resultant slab gels were washed in Triton (to remove the SDS) and then in buffer, they were laid onto underlays consisting of agarose, casein to opacify, and purified plasmin-free human plasminogen (20 µg/ml) (Lenich et al., Blood, 90:3579–86, 1997). This construct was incubated at 37° C. to develop the zymograms and photographed at times as appropriate. In zymography, the presence of plasminogen activator activity in an electrophoretic band is revealed by the local lysis of the casein in the underlay. Inhibitor complexes are seen as the higher molecular weight bands of lysis.

Figure 13A:
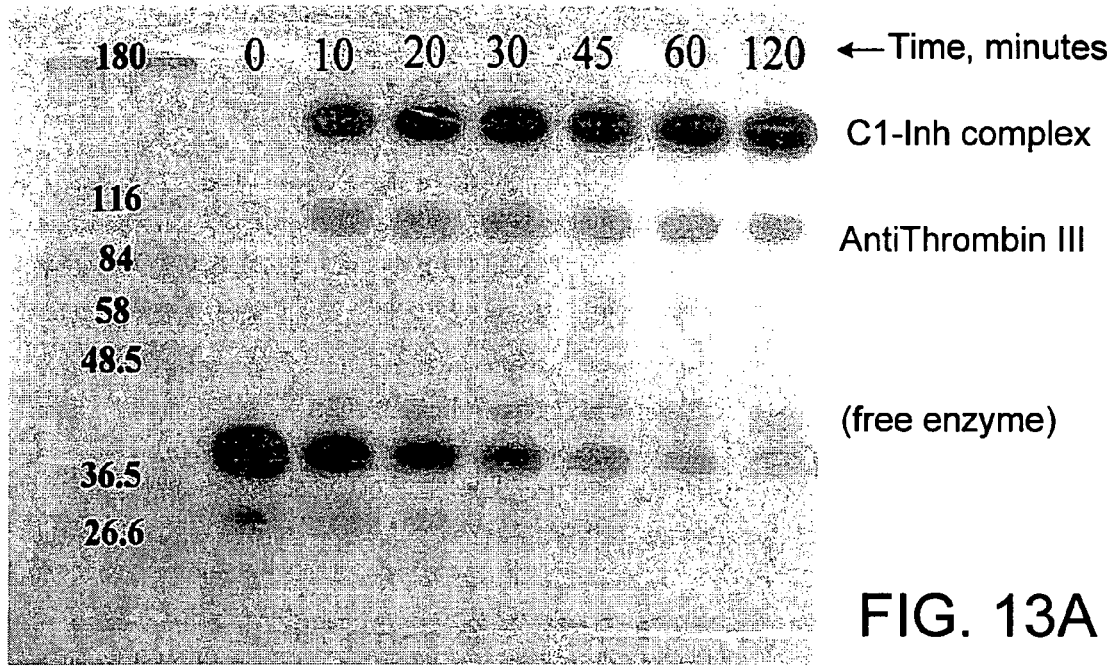
FIGS. 13A and 13B are a pair of zymograms showing the time course of the formation of inhibitor complexes of two-chain M5 (13A) and two-chain pro-UK (13B).
Figure 13B:
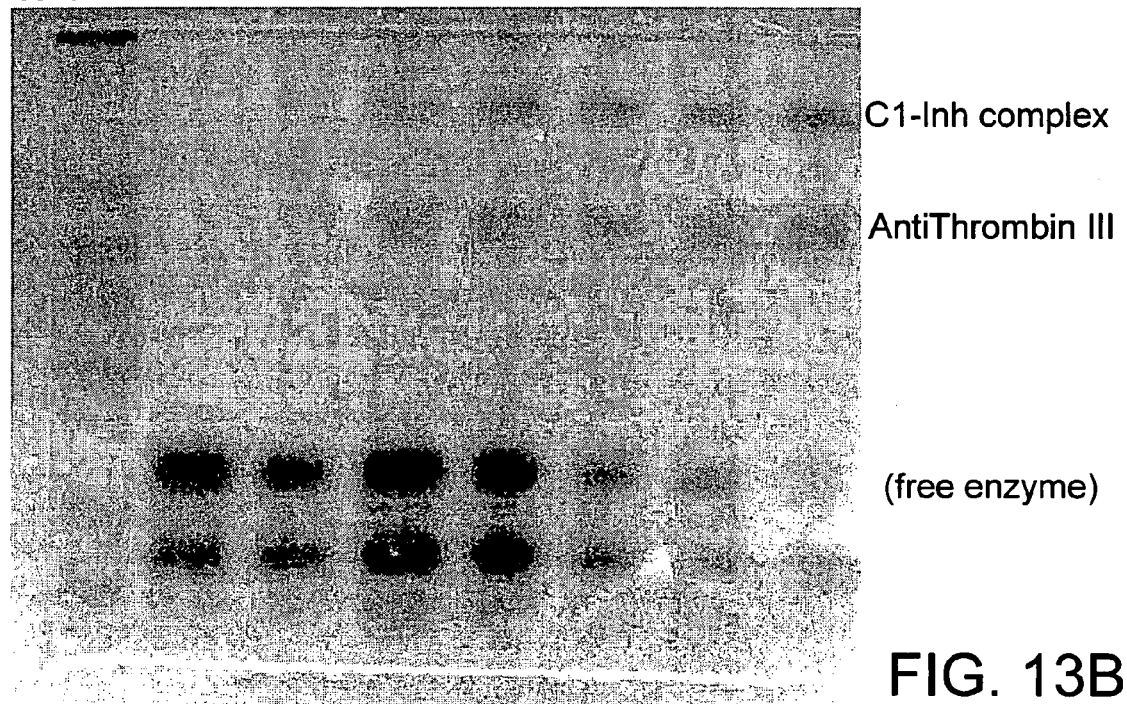

The tcM5 (FIG. 13A) was observed to be more rapidly inhibited than was the wild type tc-u-PA (FIG. 13B). For example, about half of the free M5 enzyme seems to have disappeared after 10 minutes, whereas most of the tcpro-UK is still present after 20 to 30 minutes. In addition, the C1 Inhibitor complex is prominent with tcM5 (FIG. 13A), but is barely seen with tc-uPA (FIG. 13B). These results are indicative of a greater reactivity of the active site of M5 compared to tcpro-UK. This property of more efficient inhibition of the two-chain form, which will be generated at the lysing thrombus surface, better confines plasminogen activation to this site, thus further explaining the sparing of distant hemostatic fibrin.

The principal inhibitor complexes in the plasma were identified to be C1 Inhibitor (also known as C1-Inactivator) and Antithrombin III with C1 Inhibitor appearing to be the most avid. Beyond inferences from the molecular weight of the inhibitor complexes observed in zymograms, the identity of complexes with C1 Inhibitor and with Anti-Thrombin III were confirmed by their comigration with complexes formed with commercially available purified inhibitors and by immuno-adsorption experiments using commercially available antibodies.

Example 3

Stability (Inertness) of M5 in Human Plasma Compared with Pro-UK

M5 (0–14 µg/mL) or pro-UK (0–3.0 µg/mL) was incubated (37° C.) in 1.0 mL of citrate pooled bank plasma. After six hours, 0.2 ml of a protinin (10,000 KIU/mL) was added and the fibrinogen remaining in the plasma was measured by the thrombin-clottable protein method (Swaim et al., Clin. Chem., 13:1026–1028, 1967) and compared with the baseline value.

Under these conditions, M5 remained inert and did not induce fibrinogen degradation until its concentration exceeded 8 µg/mL (see FIG. 2F), and at 10 µg/mL, 30±6% fibrinogen remained. By contrast, pro-UK induced fibrinogen degradation at a concentration greater than about 2 µg/mL (see FIG. 2C).

Example 4

In Vitro Clot Lysis by Pro-UK or M5 in Human Plasma

A previously standardized technique using radiolabeled plasma clots incubated in plasma was used (Gurewich et al., J. Clin. Invest., 73:1731–1739, 1984). $^{125}$I-labelled fibrinogen clots were prepared from 0.2 mL plasma and incubated in 4 mL plasma. A range of fibrin specific (<25% fibrinogen loss) concentrations of pro-UK (0.5–3.0 µg/mL) or M5 (0.5–14.0 µg/mL) was tested. Clot lysis was expressed as cpm of the lysis value against time. Fibrinogen was assayed (Swaim et al., Clin. Chem., 13:1026–1028, 1967) at the end of complete clot lysis or at six hours, whichever came first.

Figure 2A:
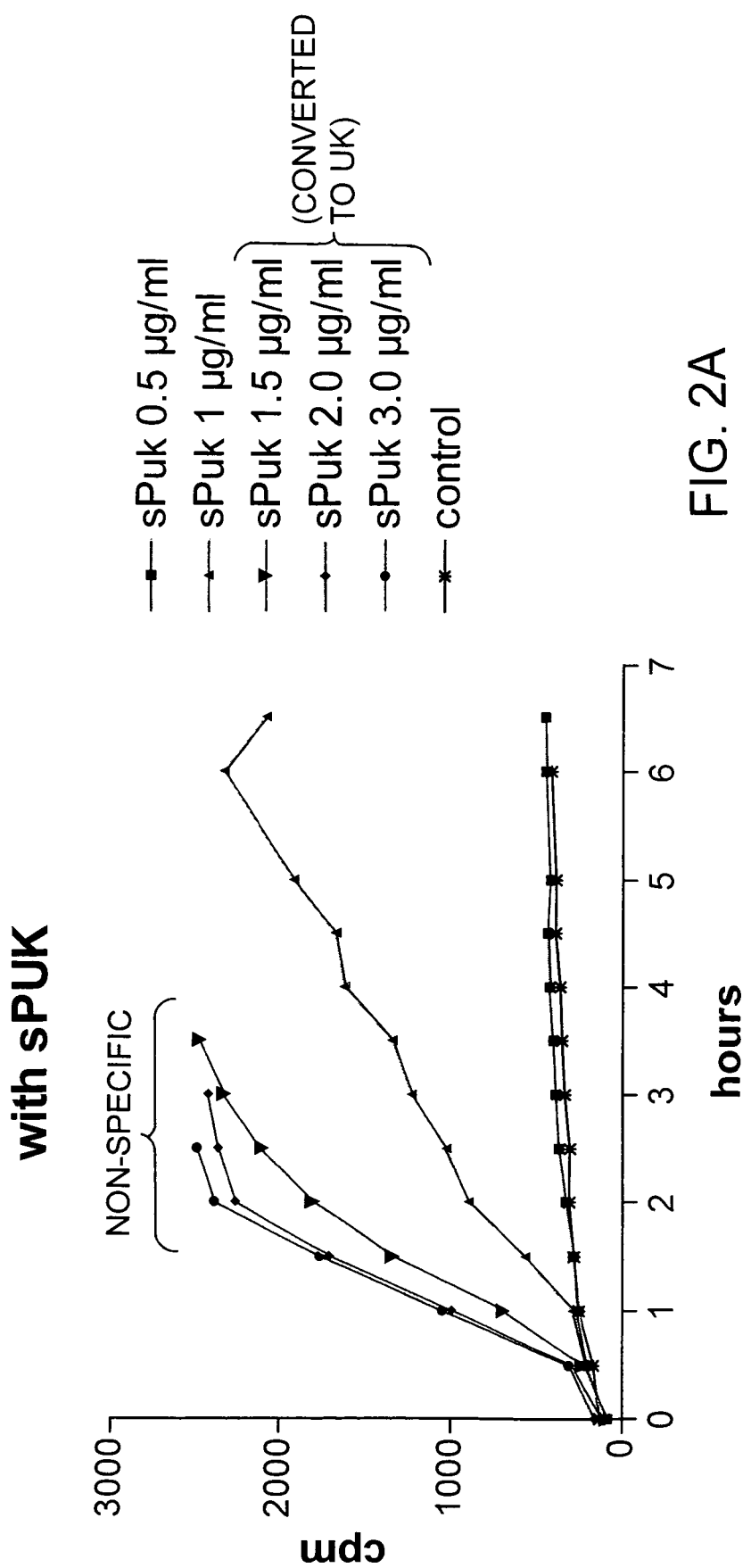
Figure 2B:
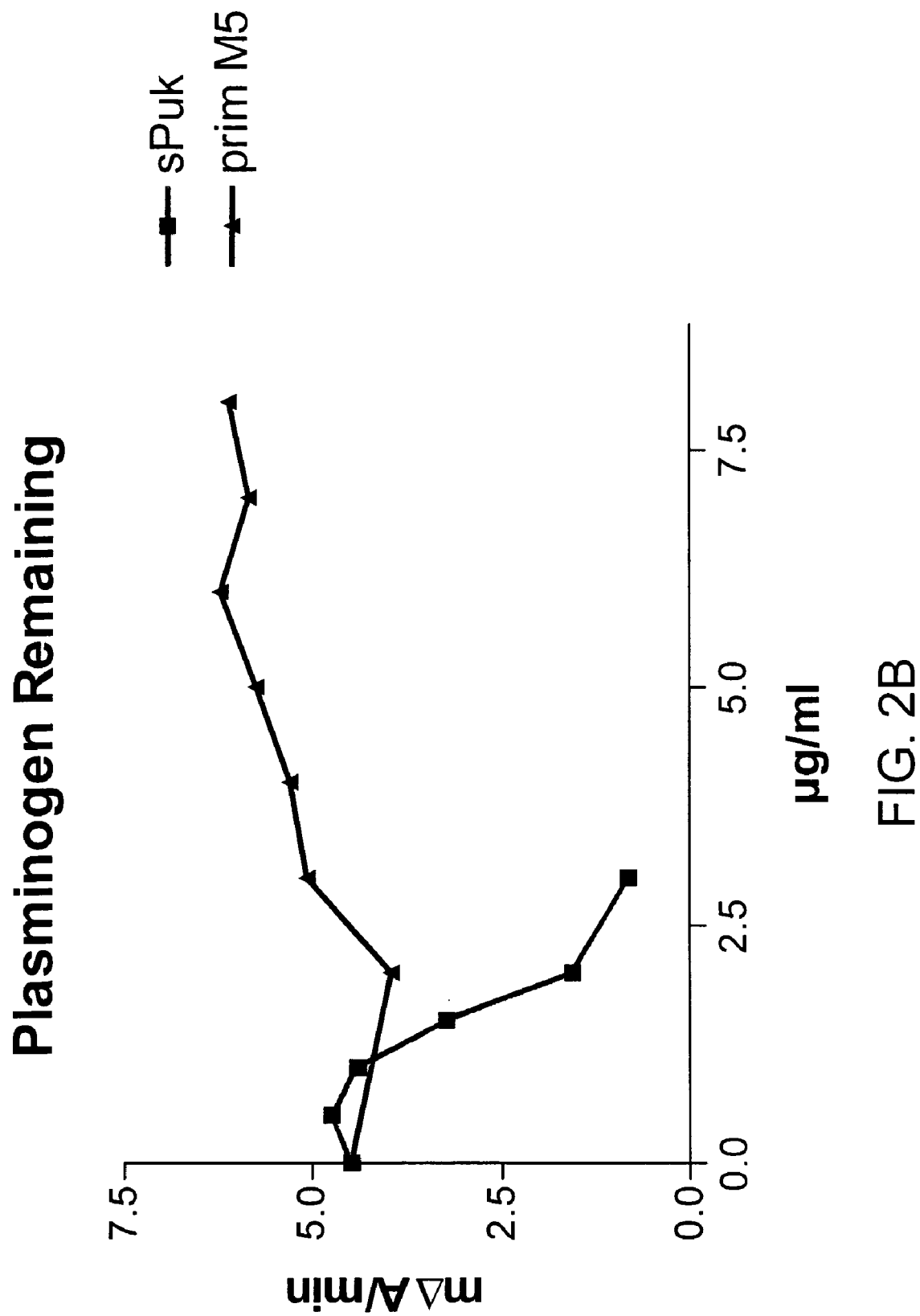
Figure 2C:
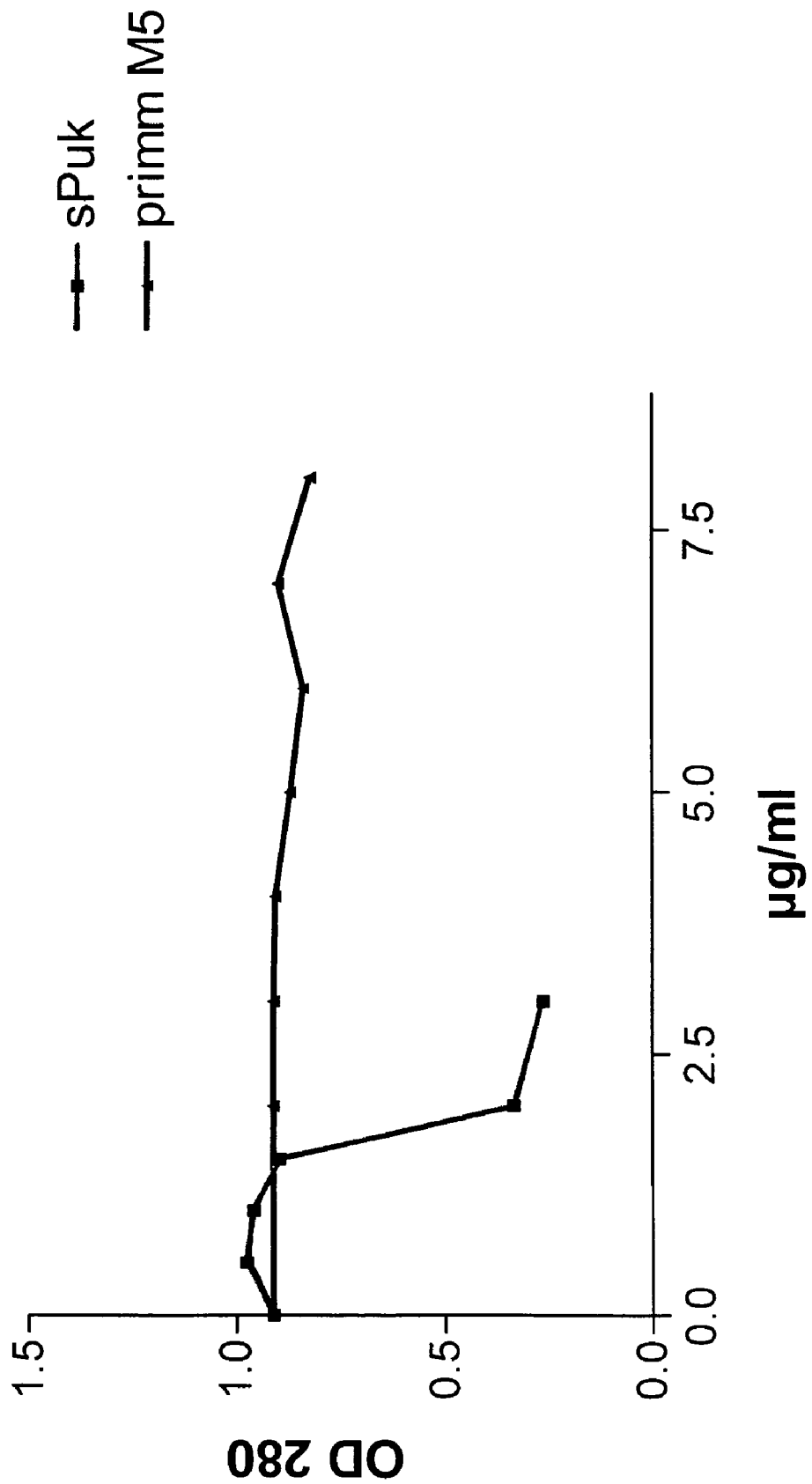
Figure 2D:
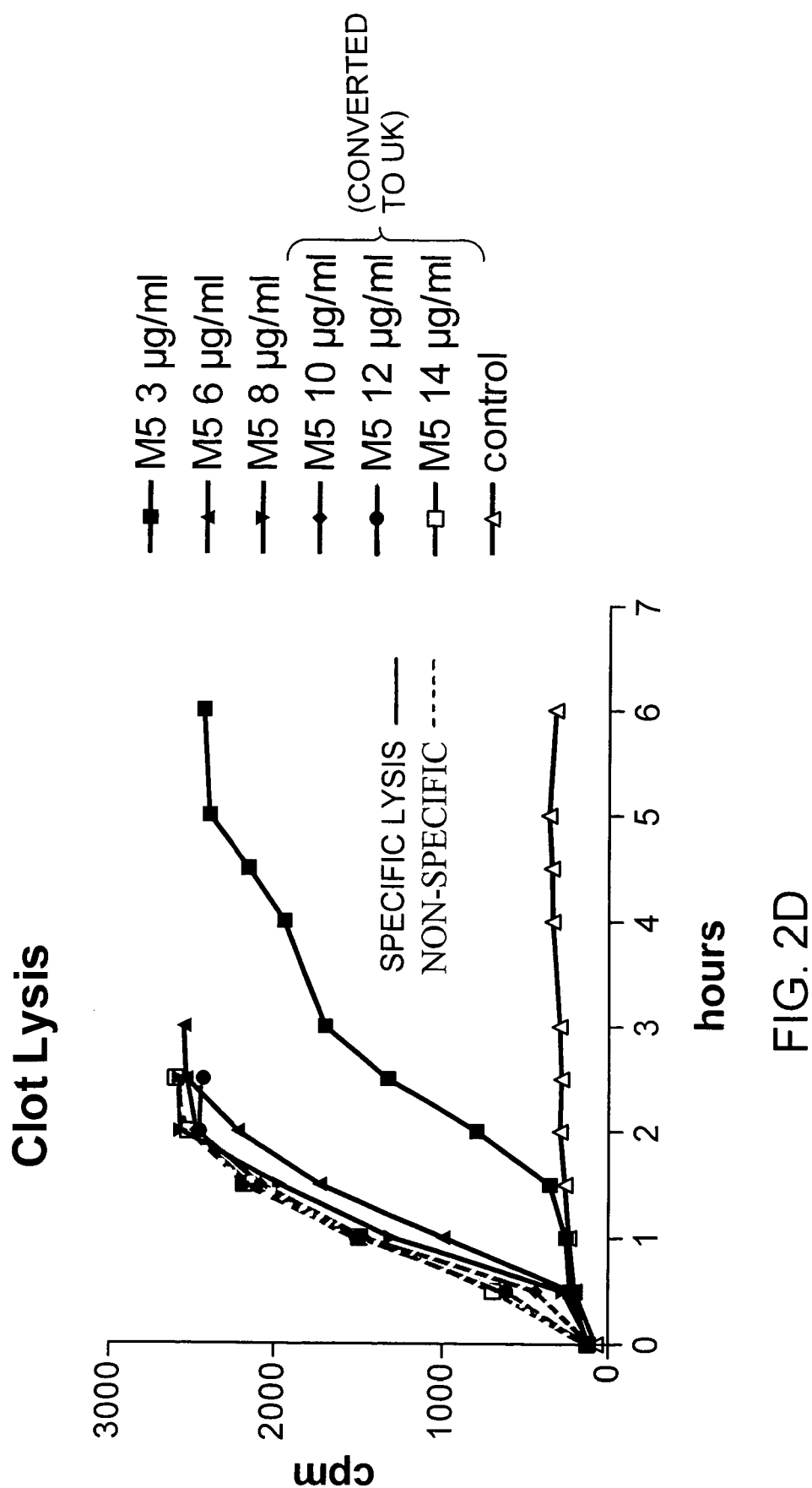

As shown in FIG. 2D clot lysis in this plasma milieu with M5 remained fibrin specific (<25% fibrinogen degradation) up to a concentration of 8.0 µg/mL, whereas as shown in FIG. 2A, the upper limit for pro-UK was 1.0 µg/mL. The maximum rate of clot lysis, determined from the slopes of the clot lysis curves, was about 40–50% per hour for pro-UK and about 70–100% per hour for M5.

FIG. 2A shows that concentrations of 0.5 and 1.0 µg/mL of pro-UK were specific, while concentrations of 1.5, 2.0, and 3.0 µg/mL were converted into UK, and thus were no longer specific. FIG. 2B shows the concentration-dependent specificity cut-off nicely (based on plasminogen remaining) for pro-UK at about 1.0 µg/mL, whereas M5 was stable, and caused no plasminogen degradation. FIG. 2C, shows the same cut-off for pro-UK based on fibrinogen remaining. Again, M5 was stable and did not degrade fibrinogen.

When M5 (2 µg/mL) was combined with a small amount (30 ng/mL) of t-PA, insufficient to induce clot lysis by itself, the lag-phase was reduced by half. This has been ascribed to the creation of new (fragment E) plasminogen binding sites by t-PA-induced lysis, which promote plasminogen activation by pro-UK and M5 (see Table 5). Therefore, fibrin-dependent plasminogen activation by M5 is similarly complementary to t-PA (promoted by fragment D) as pro-UK (data not shown).

Figure 2E:
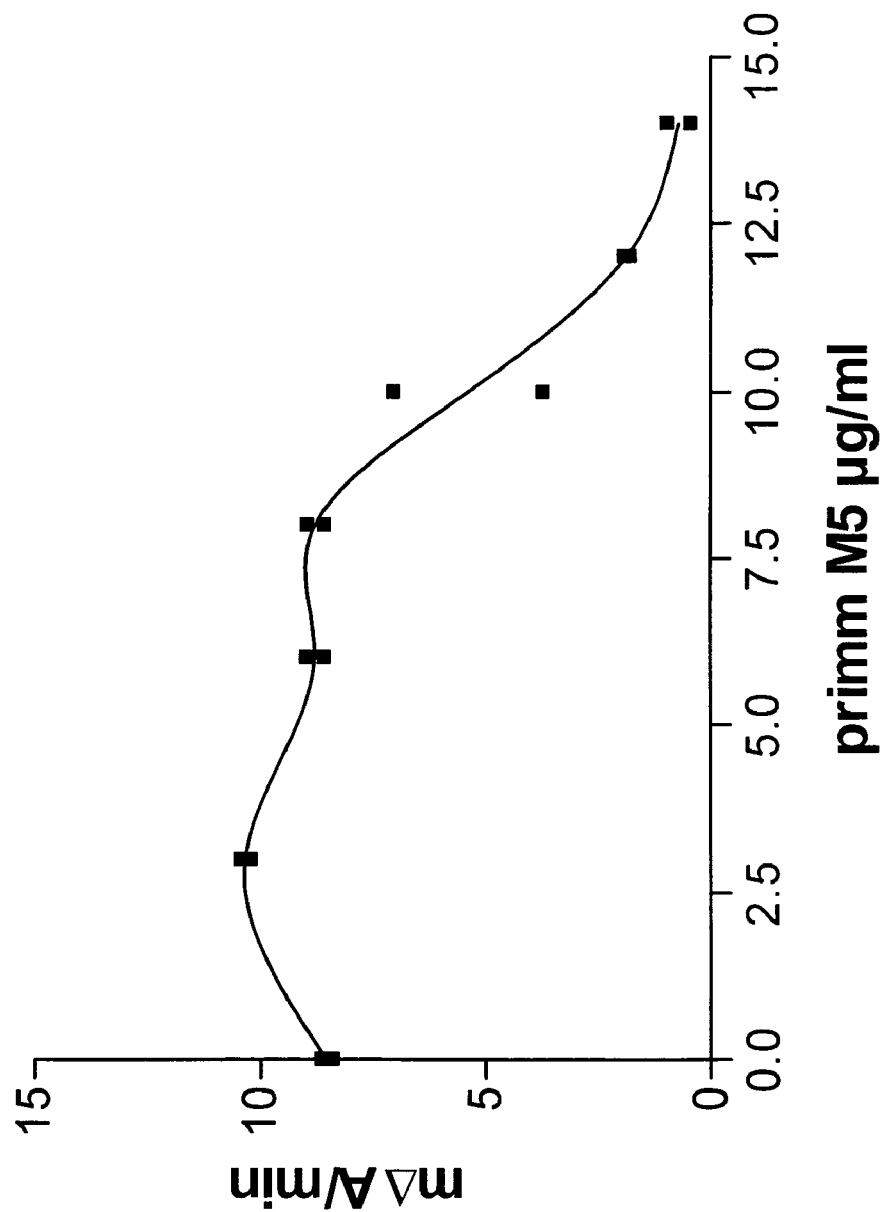

FIG. 2D shows that M5 caused specific clot lysis up to a concentration of 8.0 µg/mL, whereas concentrations of 10, 12, and 14 µg/mL caused non-specific lysis because the M5 was converted into mutant UK. What is significant, is that the rate of lysis by M5 at a concentration of 6 or 8 µg/mL was essentially the same as the rate of lysis when it because non-specific. FIGS. 2E and 2F show the results of plasminogen remaining and fibrinogen remaining, respectively. Both graphs show that M5 remains stable until a concentration of about 8.0 µg/mL.

Example 5

In Vivo Studies with M5

All procedures in animals were in accordance with the Guide for the Care and Use of Laboratory Animals (National Academy of Sciences, 1996) and were approved by the Animal Studies Committee of Nanjing University.

Clot Lysis in Anesthetized Dogs

Male, mongrel dogs weighing 10–15 kg were anesthetized with pentobarbital sodium and maintained breathing room air. An experimental model comparable to one previously used to evaluate the fibrinolytic properties of pro-UK was used (Gurewich et al., 1984, supra). Clots were formed from 1 mL native whole dog blood to which radiolabeled fibrinogen (1.9 µCi, 0.75 mCi/mg protein) and thrombin (10 units) were added. After 20 minutes, a time when clot retraction had gone to completion, the clots were washed with saline three times and then cut into small (~1 mm$^3$) pieces and injected through a 16-gauge needle into the femoral vein. After 15 minutes, a blood sample was obtained from a cannula in the contralateral femoral vein for measurement of baseline radioactivity. Then an intravenous infusion of saline or activator was started. Infusion rates of pro-UK (20 µg/kg/min) or t-PA (10 µg/kg/min), which have been reported in the literature to be both effective and fibrin-specific in dogs, were used. The t-PA infusion was limited to 60 minutes due to its high cost. The other infusions were for 90 minutes. M5 was given at infusion rates of 20, 40, and 60 µg/kg/minutes. At intervals during the infusions, blood samples were obtained for measurement of radioactivity and fibrinogen.

In these experiments, clot lysis by M5 was dose-responsive. Due to its four-fold greater stability in plasma, a three-fold higher infusion rate (60 µg/kg/h) than pro-UK was possible with M5, similar to what was found in the in vitro clot lysis experiments. As shown in the graph in FIG. 3, at this dose, M5 induced rapid lysis reaching 100% in <45 minutes. Lysis with M5 was also more efficient, since the total quantity of activator needed to achieve 50% lysis was ~600 µg/kg for M5 compared with ~1200 µg/kg for pro-UK. Higher infusion rates of pro-UK or t-PA were precluded due to non-specific effects, which cause not only excessive bleeding, but also the "plasminogen steal" phenomenon, which can inhibit clot lysis. At lower doses (40 and 20 µg/kg/min), M5 induced comparable or less clot lysis as 20 µg/kg/minute of pro-UK or 10 µg/kg/minute of t-PA (possibly due to its longer lag phase). The results are summarized in FIG. 3. The number of dogs in each group is shown in parentheses. Lysis of lung clots in dogs by M5 (20, 40, 60 µg/Kg/min) vs t-PA and pro-UK. Lysis was dose-responsive by M5 and at the highest dosage, lysed the clots twice as quickly and twice as efficiently. The doses of pro-UK and t-PA chosen were those used in the literature and found to be optimal.

Plasma fibrinogen concentration in the dogs infused with the highest dose of M5 were 72%, 65% and 52% of the baseline value at 30, 45, and 60 minutes respectively.

Assessment of Hemostasis in Dogs

In all of the dogs, bleeding from a standardized incision was measured. A 1 cm$^2$ skin incision was made over the shaved abdomen and the epidermis peeled off. One exposed superficial vessel was cut with a scalpel and the bleeding site dabbed every 30 seconds with filter paper until blood flow stopped. This was the primary bleeding time (BT), and was carried out in adjacent 1 cm$^2$ wounds at 0, 20, and 60 minutes. Total bleeding was also measured by counting the total number of standard (5×5 cm) gauze pads needed to absorb the blood oozing from the wounds. Each gauze pad was replaced after it was totally discolored by blood. This measurement represented secondary bleeding since it came predominantly from the two previous BT sites at which hemostasis had occurred. This procedure was carried out over the first 60 minutes of each infusion.

Figure 4:
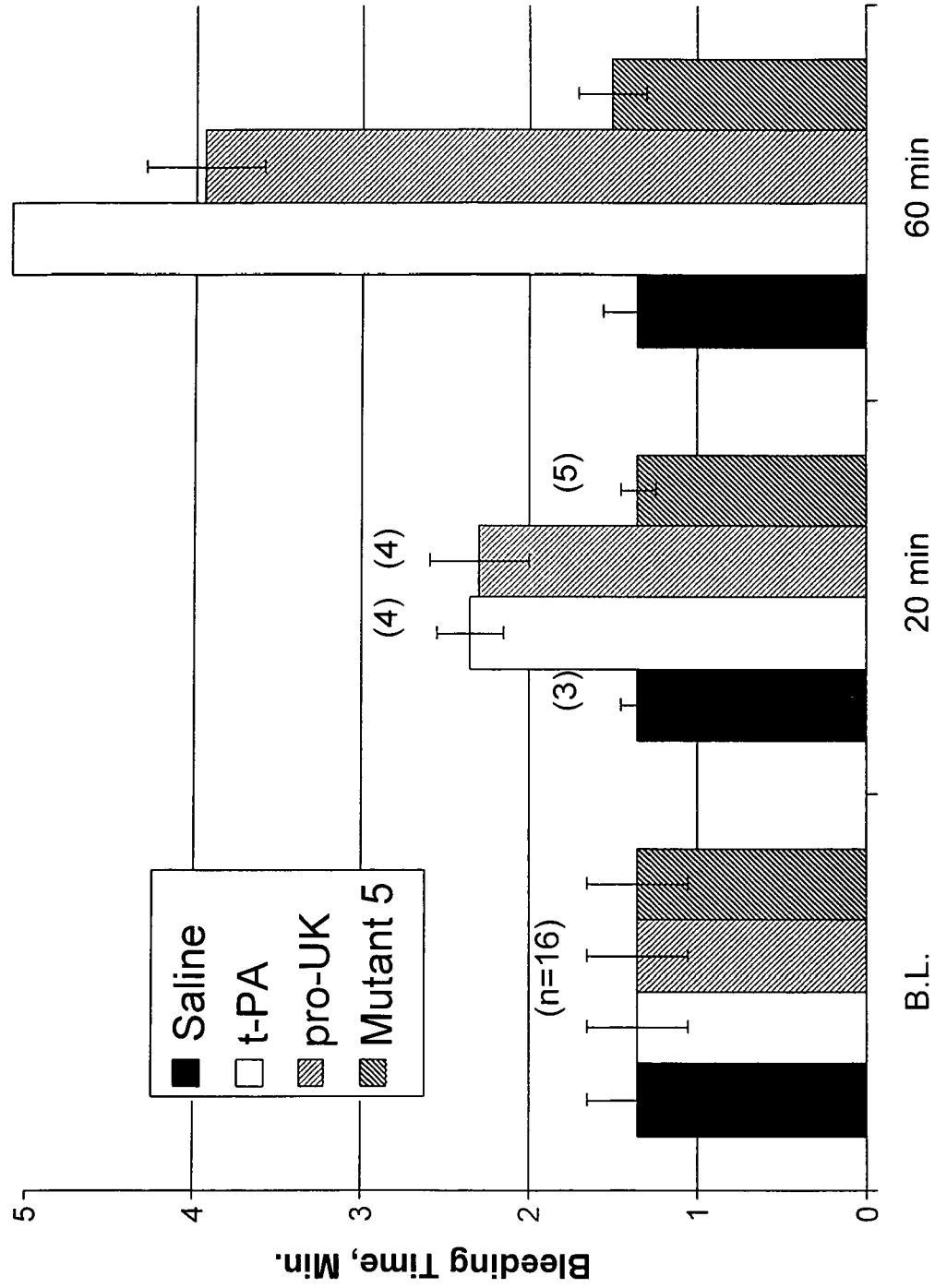
FIG. 4 is a bar graph showing bleeding time (mean±SD) in dogs (number of dogs tested is shown in parentheses) infused with saline, t-PA, pro-UK, or M5 (60 µg/kg/min).

The bar graph in FIG. 4 summarizes the results. The baseline primary BT in the 16 dogs was ~1.2 minutes and this did not change significantly during the infusion in the four saline control dogs. At 20 minutes after the start of the infusion, the primary BT in the t-PA and pro-UK infused dogs increased to ~2.4 minutes, and after 60 minutes, the t-PA animals had a primary BT>5 minutes compared with ~4 minutes for pro-UK. By contrast, in the dogs infused with the maximum dose (60 μg/kg/min) of M5, there was no increase at 20 minutes and the primary BT increased insignificantly to ~1.5 minutes at 60 minutes. Mean values±SD are shown. The number of dogs in each group is shown in parentheses.

Figure 5:
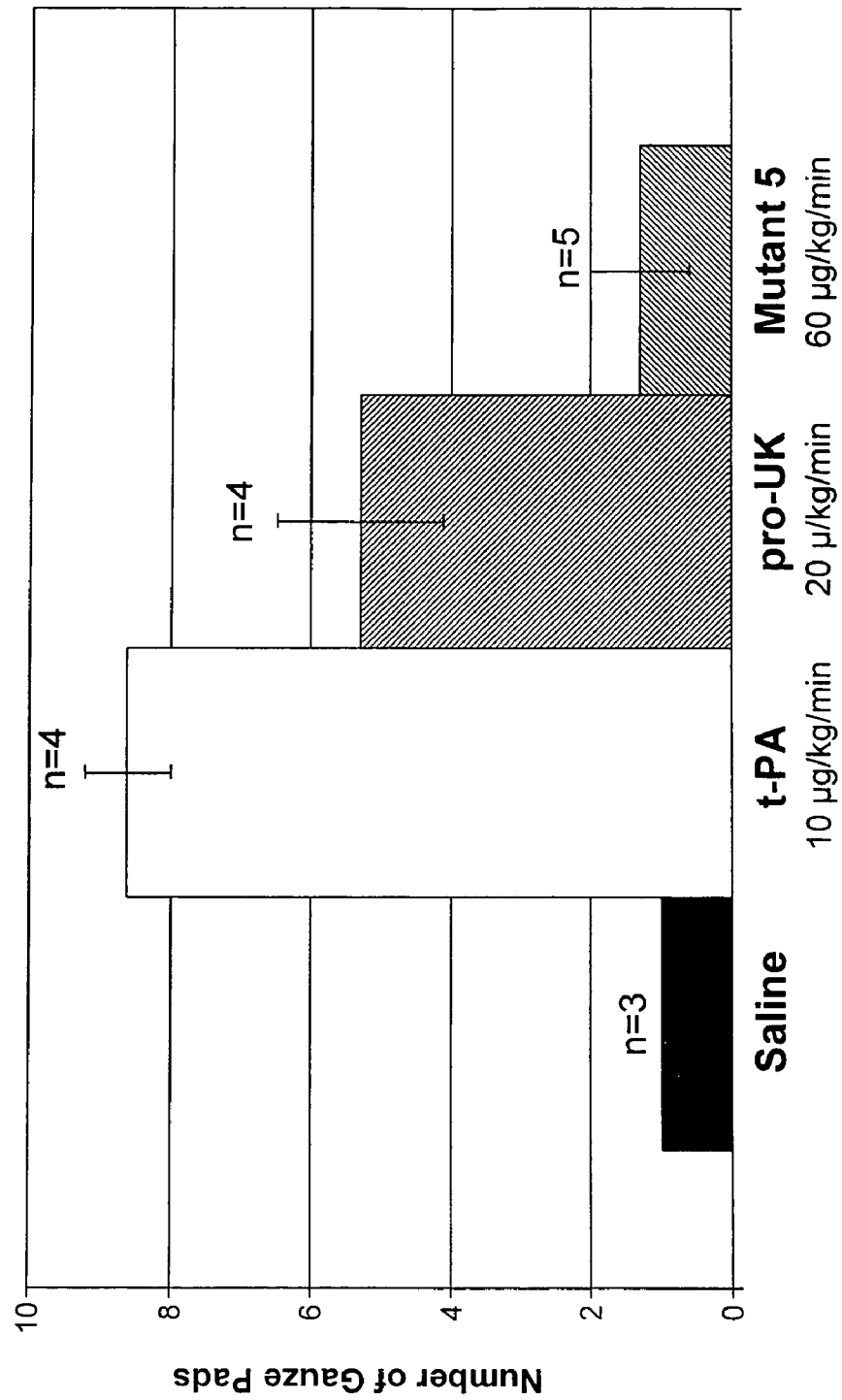
FIG. 5 is a bar graph of total bleeding (mean±SD) as measured by the total number of gauze pads used to absorb the blood from the bleeding wounds in the dogs infused with saline, t-PA, pro-UK, or M5.

The total blood loss, which was measured by the number of blood-soaked gauze pads overlying the wounds, reflected secondary bleeding since this blood loss came predominantly from rebleeding from the primary BT sites where hemostasis had occurred. As shown in the bar graph in FIG. 5, this increased more than eight-fold with t-PA, five-fold with pro-UK, but was not significantly increased by the maximum dose of M5. Mean values±SD are shown.

Clots Lysis and Hemostasis in Rhesus Monkeys

Rhesus monkeys represent a second species with a sensitivity to human pro-UK/UK comparable to that of man, in contrast to most other experimental animals. Some modification of the experimental protocol was necessary to accommodate regulations pertaining to the experimental use of monkeys, which include a requirement that their life be preserved.

Six adult Rhesus monkeys (3 males & 3 females) weighing 5.8–8.6 kg were anesthetized with intravenous sodium pentobarbital (30 mg/kg, I.V.). A polyethylene catheter was placed into each brachial vein and used for blood collection and infusion respectively. A 2 mL sample of whole blood was mixed with radio-iodinated human fibrinogen ($4.5 \times 10^6$ cpm) and thrombin (20 units) in a plastic tube, and incubated at 37° C. for 20 minutes. The whole blood clot was cut into ~1 mm³ pieces and washed with saline six times. The clots (containing $3.3 \times 10^6$ cpm) were suspended in 5 mL of saline and injected through the right brachial vein. After 30 minutes, a blood sample from the contralateral brachial vein was obtained for baseline radioactivity and then an infusion of saline (2 monkeys) or M5 (4 monkeys) was started. M5 was given at the maximum infusion rate used in the dogs (60 μg/kg/min) for 60 minutes. At intervals during the infusion, blood samples were obtained for measurement of radioactivity and fibrinogen. A BT was measured at 0, 30, 45, and 60 minutes from a cut over the lower abdomen that was 5 mm in length and 1 mm in depth using a sterile lancet. The BT was performed by the standard method using filter paper dabbing the cut every 30 seconds until bleeding stopped. Rebleeding from the BT sites where hemostasis had taken place at the earlier time points was evaluated.

Figure 6:
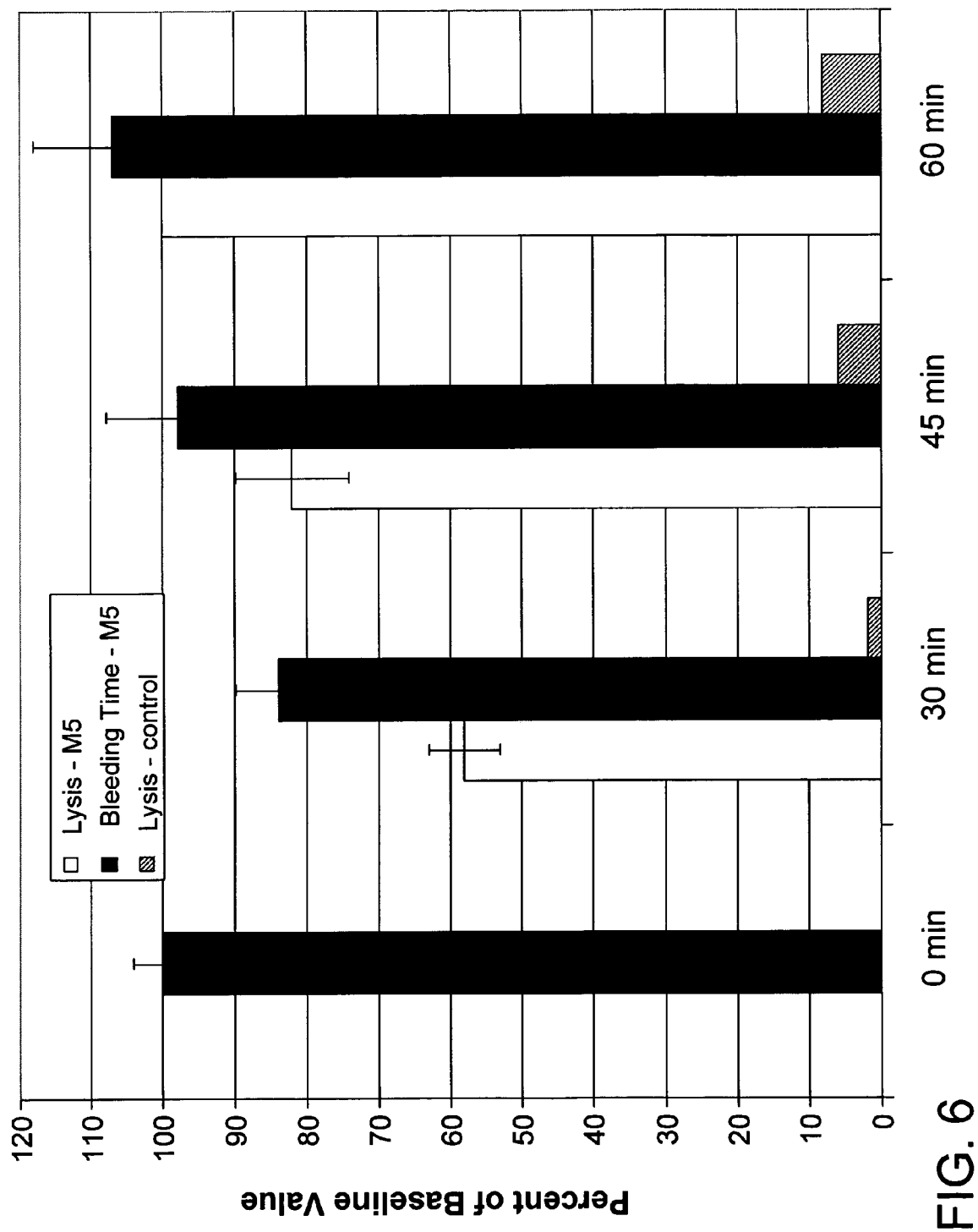
FIG. 6 is a bar graph of clot lysis, bleeding time (BT), and lysis control in four monkeys infused with M5 (60 µg/kg/min). The mean±SD values at baseline (0), 30, 45, and 60 minutes are shown. The results are presented as a percent of the baseline (0% or 100%) value. The two saline infused monkeys had ~8% clot lysis at 60 minutes (not shown).

As shown in the bar graph of FIG. 6, M5 infused at 60 μg/kg/minute induced 100% clot lysis within 60 minutes in all four monkeys compared with 8% (not shown) in the two saline infused animals. The fibrinogen concentrations at 30, 45, and 60 minutes of the infusion were 78%, 66%, and 57% of the baseline values respectively, similar to the response observed in the dogs and consistent with the observation that these two species have a comparable sensitivity to human pro-UK/UK. Mean±SD values expressed as a percent of baseline are shown.

FIG. 6 also shows the primary BT (252±2 sec), expressed as a percent of baseline (100%), at 30 minutes was reduced to 85% (215±18 sec) returning to baseline at 45 minutes, and increasing insignificantly to 108% (272±25 sec) at 60 minutes. Mean±SD values are shown. The BT in the two saline controls followed a similar pattern (not shown). Rebleeding from the BT sites at which primary hemostasis had occurred was not seen during the M5 infusions, consistent with the dogs infused with M5.

Clot Lysis of an Arterial Thrombus in Dogs

In this dog study, we studied rates of lysis of a femoral artery thrombus using the Badylak model (Badylak et al., J. Pharmacological Methods, 1988, 19:293–304). In brief, ten dogs (8–10 Kg) were anesthetized with sodium pentobarbital, a 2 cm segment of the left femoral artery was isolated, injury was induced by the infusion of hot (100° C.) water into the segment, and then the segment was filled with dog whole blood containing radiolabeled fibrinogen. After allowing time (30 minutes) for clot attachment, the ligatures were released and the intravenous infusions begun. T-PA was infused at a rate of 10 μg/Kg/min. and M5 was infused at a rate of 60 μg/Kg/min. Both infusions were for 90 minutes. Lysis was measured by the reduction in radioactivity measured by a probe fixed above the femoral artery thrombus, and flow rates were measured with a flow meter.

The infusion rate of t-PA used herein was the one shown in the literature to give optimal lysis (Young et al., Thrombosis and Haemostasis, 1995, 74:1348–1352). At higher infusion rates of t-PA, non-specific effects begin to predominate, which are associated with plasminogen consumption ("plasminogen steal" phenomenon), which impairs lysis due to the loss of substrate.

Figure 14A:
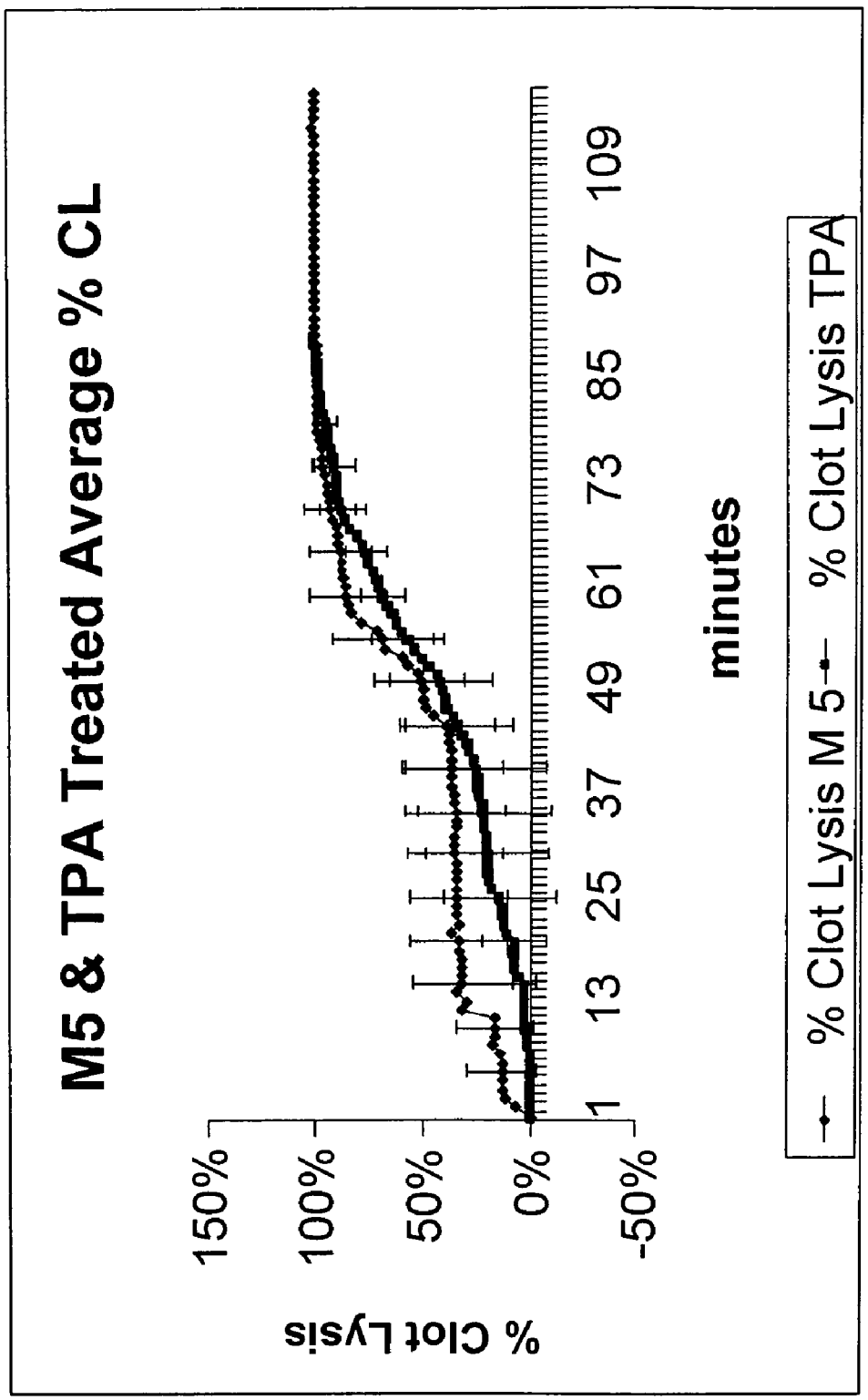
FIG. 14A is a graph showing percentage of clot lysis by M5 and t-PA over time in an arterial thrombus dog model.
Figure 14B:
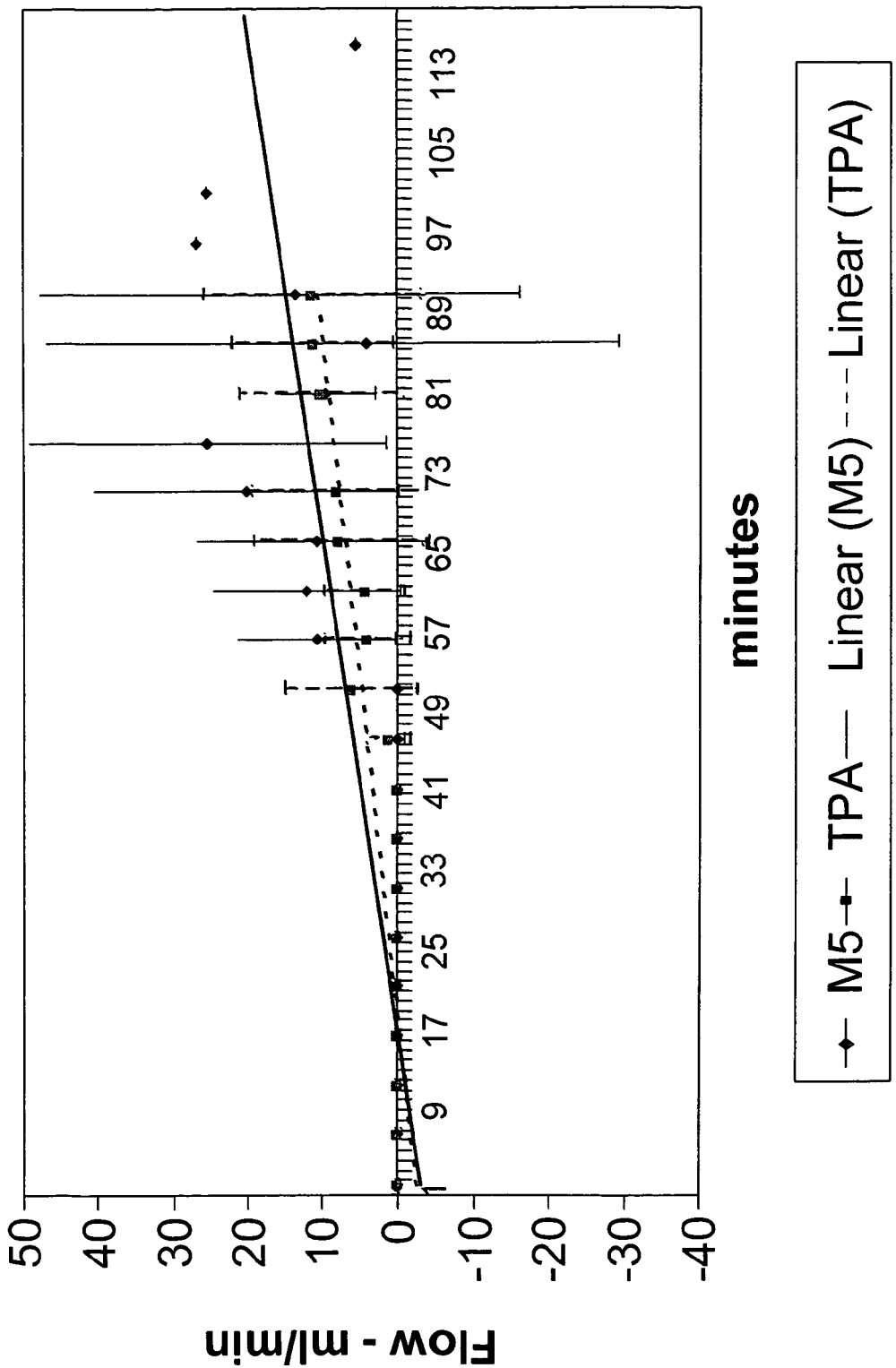
FIG. 14B is a graph showing flow averages of M5 and t-PA over time in an arterial thrombus dog model.

The mean and standard deviations for lysis and reflow are shown in FIGS. 14A and 14B. As shown in FIG. 14A, M5 achieved 30% clot lysis within about 13 minutes, whereas it took tPA over 45 minutes to reach the same level. Both M5 and tPA reached 100% clot lysis after about 85 minutes. As shown in FIG. 14B, the reflow rate was more rapid in the M5-infused dogs compared with the t-PA-infused dogs. In FIG. 14B, "linear M5" and "liner t-PA" refers to their mean flow rates. These results indicate that M5 provided significantly faster lysis and reflow than did t-PA.

Summary of In Vivo Results

Figure 3:
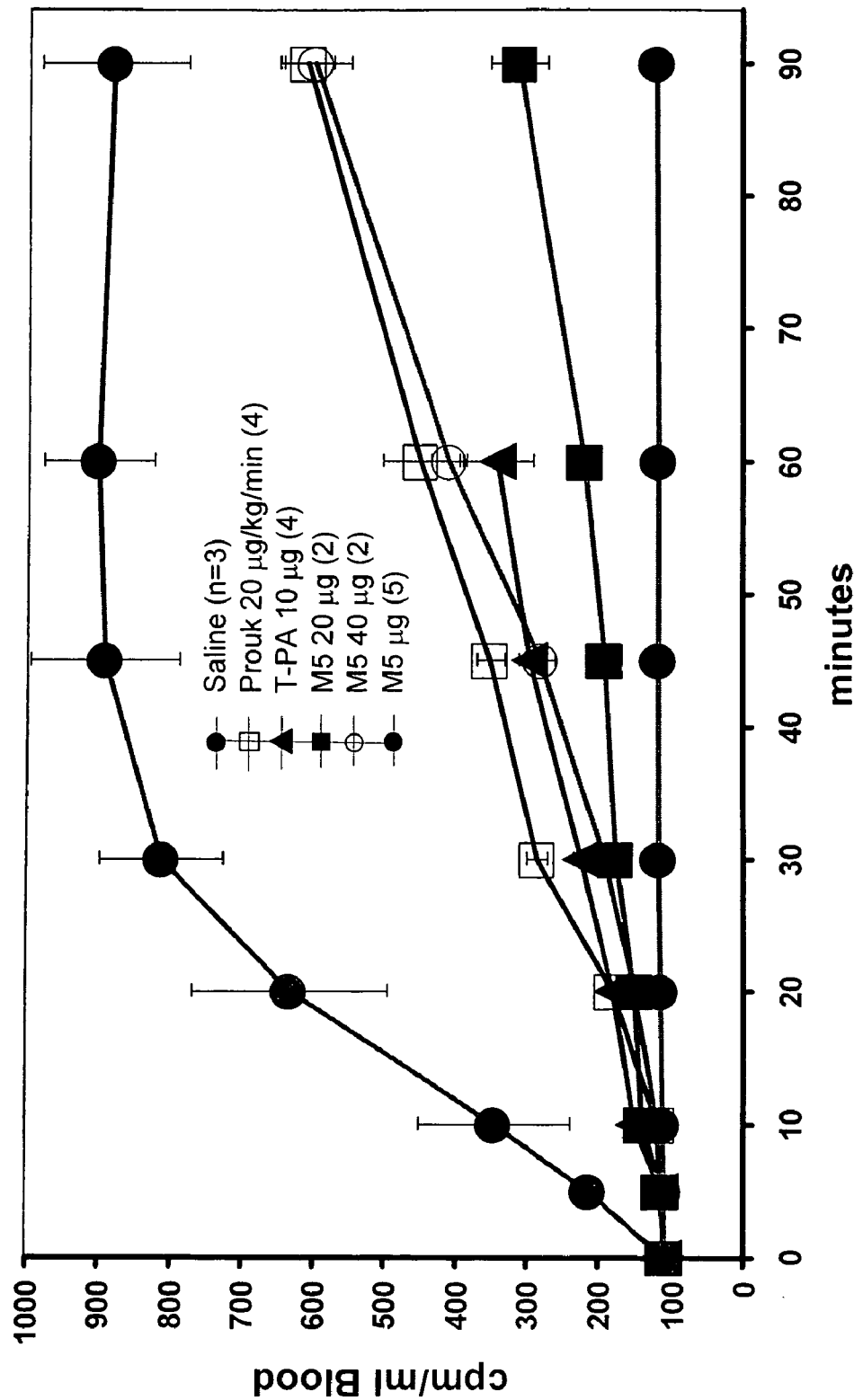
FIG. 3 is a graph representing in vivo lysis of $^{125}$I-labeled whole blood clots in the dog. The radioactivity in plasma samples (mean±SD) obtained at intervals is shown. The number of dogs in each group is shown in parentheses and the infusate (saline, pro-UK, t-PA, or M5) and infusion rate (µg/kg/min) are indicated. Pro-UK cannot be given at the infusion rate of 60 (µg/kg/min) because it will immediately convert to UK and cause bleeding and consume plasminogen, the substrate needed for lysis. This results in less lysis ("plasminogen steal" effect).

A rapid lysis of clots by M5 was observed in dogs. In parallel with the in vitro findings, M5 was less efficient than pro-UK or (t-PA) at comparable doses, but at a three-fold higher infusion rate, M5 induced 100% clot lysis within 45 minutes compared with 30% or less by the other two activators. The rapidity of lysis by M5 made it also more efficient, since the total amount of activator needed to induce lysis of 50% the clots was only ~600 μg/kg for M5 compared with ~1200 μg/kg for pro-UK (FIG. 3). Higher infusion rates with pro-UK were precluded by its more ready conversion to UK, resulting in non-specific effects. Since the lysis properties of M5 in vitro and in vivo were comparable and reflect the catalytic changes induced by the mutation, it reasonably expected that these properties will also be seen upon administration to humans.

Some fibrinogen degradation was observed at the highest dose of M5, reflecting non-specific plasminogen activation. However, this was insufficient to interfere with hemostasis, since no significant increase in either the primary bleeding time (FIG. 4) or total blood loss (FIG. 5) occurred. The latter was predominantly related to rebleeding at the primary BT sites and therefore corresponds to secondary bleeding, suggesting that hemostatic fibrin was spared by M5. By contrast, the primary BT and secondary bleeding increased four to eight-fold in the pro-UK and t-PA treated dogs, whereas clot lysis was at least two-fold less effective in these animals. It is noteworthy that bleeding has not been well correlated with non-specific plasminogen activation and that some highly fibrin-specific activators interfere significantly with hemostasis (Montoney et al., Circulation, 91:1540–1544, 1995).

It may be postulated that bleeding during fibrinolysis reflects a vulnerability of hemostatic fibrin to the activator.

The most bleeding occurred with t-PA, which is consistent with the paradoxically higher rate of intracranial bleeding associated with this activator. The infusion rate at which intravascular clot lysis by M5 was the most rapid induced little or no rebleeding at the BT sites where hemostasis had occurred. Therefore, this hemostatic fibrin in dogs and monkeys appeared to be resistant to the thrombolytic properties of M5. These findings attest to the presence of certain apparent differences between fibrin in a thrombus and hemostatic fibrin. Some differences may arise from the fact that only a thrombus occludes a vessel. Stasis can trigger the local release of t-PA from the endothelium and facilitate its binding to the thrombus, initiating some fibrin degradation. As a result, new plasminogen binding sites are exposed. Plasminogen bound to these new sites (fibrin fragment E) is selectively activated by pro-UK, a property retained by M5. By contrast, fibrin fragment D (intact fibrin) promotes plasminogen activation by t-PA. This difference may help explain the lower BT and blood loss by pro-UK than t-PA. Since M5 is more stable in blood than pro-UK, this selective fibrinolytic mechanism is better preserved at pharmacological doses.

Example 6

Acute Myocardial Infarction (AMI)

A patient arrives at the Emergency Room (ER) of a hospital with symptoms of AMI. A loading dose (20–40 mg) of M5 is immediately injected (due to its safety, delay in treatment until triage and diagnosis is confirmed is not necessary). Thereafter, an EKG is taken and blood tests are obtained to validate the diagnosis. If AMI is confirmed, an infusion of M5 (100–120 mg/h) is started immediately. Then a catheterization team is assembled, the angioplasty room is prepared, and the patient is transported there for this procedure. Since experience shows that this takes 60–90 minutes, thrombolysis will have been completed by the time the angiogram is taken. If significant stenosis due to atheromatous plaque is present, angioplasty and stent placement is performed, but this may be unnecessary. Thus M5 leads to more accurate diagnosis and proper treatment.

This early treatment is especially important in diabetic patients, because the diabetic myocardium tolerates ischemia significantly less well than the non-diabetic, making early reperfusion critical. About 30% of AMI is in diabetics and is associated with a significantly higher mortality. In addition, thrombolytics are rarely given to patients over the age of 75 because of higher rates of hemorrhagic complications in this age group. At the same time, the mortality from AMI is much higher in the age group and the therapeutic benefit of therapeutic thrombolysis is correspondingly higher. Thus, pro-UK flexible loop mutants such as M5 are especially beneficial in diabetics and older patients.

Example 7

Angioplasty/Stent Procedures

A patient arrives at a hospital with new onset angina pectoris, unstable angina, or exacerbation of existing angina. All of these clinical scenarios are consistent with ischemia due to new compromise of perfusion in one of the coronary arteries, which is invariably related to some clotting on an athereromatous plaque.

A bolus of M5 (as in Example 6) is given and an infusion is started. After further evaluation (triage) an interventional procedure is elected. Preparations for an elective angioplasty/stent are then made. Since it has been shown that removal of thrombus improves the outcome of these procedures, this pretreatment with M5, which is not possible with existing thrombolytics, represents a significant improvement over current management of these patients.

Example 8

Stroke

A patient with arterial fibrillation arrives at the ER 3 hours after the sudden onset of hemiplegia. A bolus of M5 and infusion (as in Example 6) are immediately started.

A CT scan of the head is performed showing ischemia, but no hemorrhage. Current evidence indicates that when reperfusion is achieved within 6 hours of a stroke, significant recovery of brain function is achieved. This is currently not possible because the benefits of t-PA (the only drug approved by FDA for the U.S.) are limited to 3 hours.

Example 9

Post-Operative Usage

A post-operative patient sustains a major pulmonary embolus (a not uncommon post-operative complication). M5 is administered by infusion and/or bolus at the dosages indicated in Example 6.

Note, in the post-operative period (2–3 weeks) all currently available thrombolytic drugs have been strictly contraindicated due to an extremely high risk of major hemorrhage, related to lysis of hemostatic fibrin in the surgical wound. Therefore, this patient would be denied thrombolytic treatment, which in the case of a major embolus would be life-saving. Use of M5, on the other hand, spares hemostatic fibrin, and may be used.

Example 10

Peripheral Artery Disease

A patient enters a hospital with worsening of his intermittent claudication (due to peripheral artery disease). Although, with these patients, arterial disease is largely atherosclerotic, there is often a significant clot overlay, which is susceptible to lysis. These patients have not been given the benefit of currently available thrombolytic drugs because the available drugs have been considered too toxic because of the bleeding effects. The safety of M5 can open up this indication, as it can be tried with little or no risk. If it does not work, surgery can always be a second resort. Therefore M5 can be administered as in Example 6.

Example 11

Refractory Angina Pectoris

A patient with refractory angina pectoris is treated with a dosage of M5 (150 mg) infused over one hour, 3 times per week for 12 weeks.

Example 12

Clearing of Dialysis Catheter

In all patients on chronic dialysis, blocked catheters due to accumulation of fibrin material is a recurrent problem. To deal with this problem, 5000 units of two-chain M5 (0.03 mg) are instilled to clear each port.

The present FDA approved labeling is for 0.05 mg UK (Abbokinase®), but when this was taken off the market, it was replaced by 1 mg of t-PA. Abbokinase® was recently reintroduced to the market, but it is less potent than mutant UK, such as tcM5. Abbokinase® is also a low molecule weight form, which is a less efficient plasminogen activator than high molecular weight UK. The use of low molecular weight mutant UK (e.g., LMW tcM5) would significantly improve results compared to the use of dialysis catheters, the dose is 5,000 IU per port. This is equivalent to 0.025–0.05 mg and this induces the same hemodialysis blood flow rate as 1 mg of t-PA.

Example 13

Preparation of M5

Competent cells of strain BL21/DE3 RIL were prepared using a calcium chloride procedure of Mandel and Higa (Mol. Biol., 53:154, 1970). 200 µl of a preparation of these cells at $1 \times 10^9$ cells per milliliter was transformed with 2 µl of plasmid pET29aUKM5 that encodes M5 (approximate concentration 5 µg/ml). Transformants were selected on plates of L-agar containing 30 µg/ml kanamycin.

Figure 10:
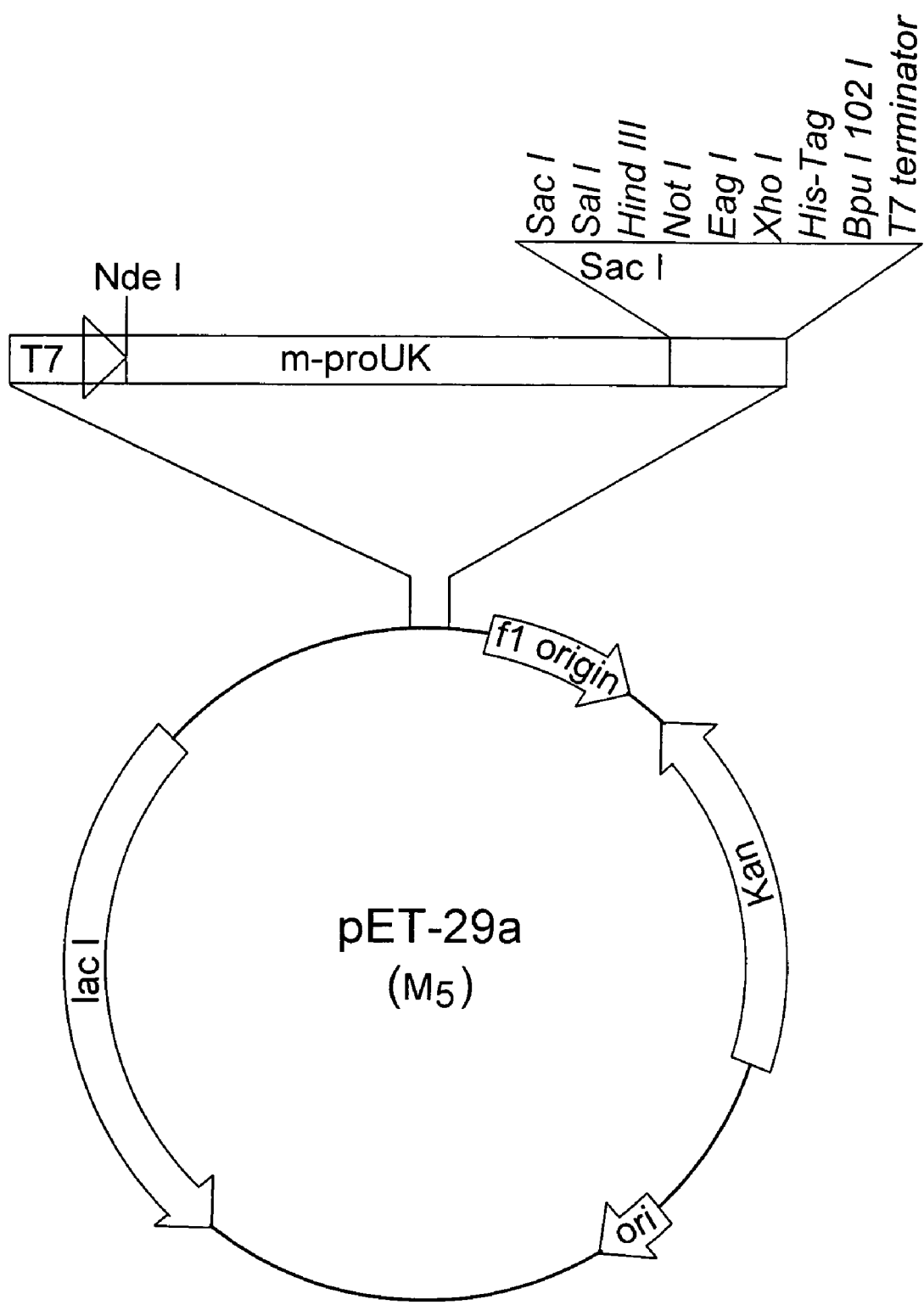
FIG. 10 is a representation of plasmid pET-29aUKM5 that can be used to make M5.
Figure 11:
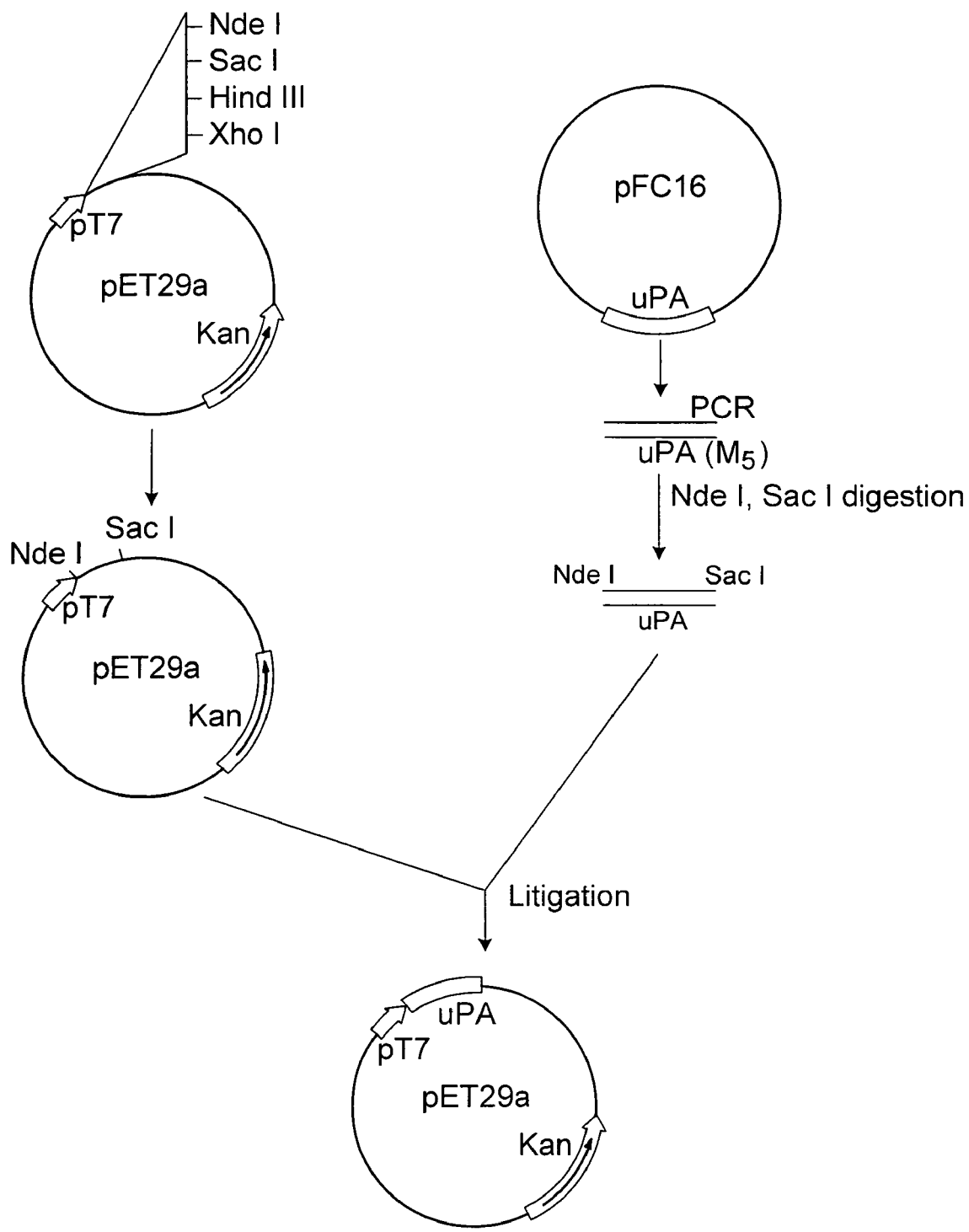
FIG. 11 is a representation of a method to construct the pET-29aUKM5 plasmid.

Plasmid pET29aUKM5 was made starting with plasmid pET29a (Novagen) shown in FIG. 9. As shown in FIGS. 10 and 11, to construct pET29-u-UKM5 for the expression of pro-UK (M5), the pro-UK (M5) gene was amplified from plasmid pFC16 by the polymerase chain reaction using the following primers:

```
                                              (SEQ ID NO:1)
Primer 1 (5' GAG GAT TAC ATA TGA GCA ATG AGC 3'), (SEQ ID NO:2)
Primer 2 (5' CTG GGG ACC GAG CTC TCA GAG, GGC CAG GCC ATT 3')

(SEQ ID NO:3)
Primer 3 (5' GGC TTT GGA CAC GAG AAT CTT ACC GAC TAT CTC 3')

(SEQ ID NO:4)
Primer 4 (5' AGA ATT CTC GTG TCC AAA GCC AGT GAT CTC AC 3')
```

Primer 3 and Primer 4 were used to mutate $Lys^{300} \rightarrow His$. Primer 1 and Primer 2 were used to incorporate NdeI and SacI restriction sites immediately 5' to the first codon and immediately 3' to the stop codon of pro-UK cDNA, respectively. The amplified pro-UK M5 (M5) gene was digested with NdeI and SacI, purified, and ligated with the large fragment of NdeI-SacI-digested pET29a. The sequence of the M5 coding region was confirmed by DNA sequencing.

Two small colonies were streaked with wooden toothpicks (each as three streaks about 1 cm long) onto L-agar containing the same antibiotic. After 12 hours of incubation at 37° C., portions of the streaks were tested for M5 production by inoculation onto 10 ml of LB medium (containing kanamycin at a concentration of 30 µg/ml) and incubated overnight at 37° C. The following day, the cultures were diluted 1:100 in M9 medium, containing the same concentration of kanamycin, and incubated for 6 hours at 37° C. Total cell proteins from 250 µl aliquots of culture (O.D.$_{550}$=1 to 1.5) were analyzed by sodium dodecylsulfate polyacrylamide gel electrophoresis (SDS-PAGE) as described in Laemmli, Nature, 227:680, 1970. A major protein band having a molecular weight corresponding to that of non-glycosylated M5 (45,000 daltons) was observed for the two independent samples.

FIG. 12 shows the SDS-PAGE results. Lane 1 includes molecular weight standards. Lanes 2, 3, and 4 show the results of the supernatants at an OD of 1.5. Since M5 is an insoluble protein, we did not expect to find M5 in the supernatant, and found none. The band at about 45 kDa is a soluble host protein. Lane 2 contains BL21(DE3)RIL [pET29a], which lacks the M5 encoding gene. Lane 3 contains BL21(DE3)RIL[M5-PUK], which has the M5 encoding gene, and the RIL strain, but since M5 is insoluble, we found none in this lane. Lane 4 BL21(DE3) [M5-PUK], which has the M5 encoding gene, but not the RIL strain. Again, there was no M5 in the supernatant.

Lanes 5, 6, and 7 show the results of the pellet ("inclusion bodies"), again at an OD of 1.5. Lane 5 contains BL21(DE3) RIL[pET29a] (no M5 encoding gene), and as expected, it shows no M5. Lane 6 contains BL21(DE3)RIL[M5-PUK], which has the M5 encoding gene, and the RIL strain, and shows a very high level of M5. Lane 7 contains BL21(DE3) [M5-PUK], which has the M5 encoding gene, but not the RIL strain. This strain does produce some M5, but not nearly as much as the RIL strain.

A set of streaks corresponding to colony no. 2 (clone 2) was chosen arbitrarily for further characterization and then selected as an M5 producing strain.

Example 14

Testing of Alternate Host Cells

Using the procedure described herein and in Example 13, several additional E. coli host strains were screened with the objective to isolate a transformant strain able to produce M5 at high levels. Plasmid pET29aUKM5 in the following strains: BL21/DE3, BL21/DE3 pLys, JM109/DE3, and HB 101/DE3. None of these strains, when transformed with plasmid pET29aUKM5, was able to yield high quantities of the M5 polypeptide as seen with the host strain BL21/DE3 RIL, indicating that indeed the combination of the specific expression plasmid with strain BL21/DE3 RIL is an important combination to obtain high quantities of M5. For example, the following yields were obtained:

| Host strain | Productivity |
| --- | --- |
| BL21(DE3) RIL | 4.12 grams/liter |
| BL21(DE3) | 0.91 grams/liter |
| BL21(DE3)pLys | 0.82 grams/liter |

The productivity is expressed as quantity of M5 polypeptide as measured by SDS PAGE analysis and quantified against a standard of pro-UK. Thus, it is clear that the combination of the specific plasmid and its Phage T7 promoter sequences and strain BL21/DE3/RIL provides a far greater yield than even other type B strains. This data quantifies the results seen in Lanes 6 and 7 of FIG. 12. Although the *E. coli* type B strain BL21(DE3) produces some M5, the BL21(DE3)RIL strain produces about 4.5 times as much M5.

Example 15

Fermentation of the Host Cells

Transformed bacterial cells are cultured at high biomass in appropriate fermentors as follows. A first fermentation phase was carried out in Erlenmeyer flasks to obtain a seed culture large enough to inoculate the production stage (second fermentation stage). One vial of working cell bank (0.1 ml) was diluted in 100 ml of sterile EC1 medium (details are provided in Table 4 below) and grown at 37° C. overnight with the agitation of 220 rpm.

The working cell bank was made of a glycerol suspension of an overnight LB culture containing kanamycin at 30 µg/ml and chloramphenicol at 30 µg/ml of the M5 producing strain (BL21/DE3 RIL carrying plasmid pET29aUKM5).

TABLE 4

Medium EC-1

| Per liter: | |
|---|---|
| Glucose | 10 g |
| Yeast extract | 1 g |
| (NH$_4$)2HPO$_4$ | 2 g |
| K$_2$HPO$_4$ | 6.75 g |
| MgSO$_4$ × 7H$_2$O | 0.7 g |
| Citric acid | 0.85 g |
| TMS (see below) | 5 ml |
| TMS: Per liter of 5M HCl | |
| FeSO$_4$ × 7 H$_2$O | 10 g |
| ZnSO$_4$ × 7 H$_2$O | 2.25 g |
| CaCl$_2$ × 2 H$_2$O | 2 g |
| CuSO$_4$ × 5 H$_2$O | 1 g |
| MnSO$_4$ × 5 H$_2$O | 0.23 g |
| Na$_2$B$_4$O$_7$ × 10 H$_2$O | 0.23 g |
| (NH$_4$)$_6$MO$_7$O$_{24}$ | 0.1 g |

A second fermentation stage includes the following steps:

(1) 20 ml of the seed culture, prepared in the Erlenmeyer flask, was added to 2.0 liters of EC-1 medium in a fermentor;

(2) the pH in the fermentor was kept at 6.8 using a solution of 28% (v/v) ammonia water;

3) D.O. was maintained at 40% of air saturation by increasing the agitation speed and by changing the percentage of pure oxygen;

(4) the temperature of fermentation was kept at 35° C.; and (5) a nutrient feeding solution (described in further detail in Table 5 below) was added exponentially when all the glucose initially present is consumed (usually after 8 hours), following the equation V=Vo $e^{0.18t}$, where V=volume of feeding solution added (ml/h), Vo=1/100 of the starting fermentation medium (ml), and t=time of fermentation after the start of the feeding phase (hours).

TABLE 5

| Feeding Solution | |
|---|---|
| Per liter: | |
| Glucose | 400 g |
| Yeast extract | 100 g |

In this method, gene expression was induced by adding IPTG at a final concentration of 1.2 mM, when the fermentation reached a cell density of 90 OD$_{600}$.

The post-induction fermentation was prolonged for 6 hours to allow the cells to produce M5. Samples of 0.5 ml were removed every 2 hours for analysis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a person with symptoms of stroke, the method comprising:
   (a) determining that the person potentially has had a stroke based on observing one or more symptoms of stroke to make an initial diagnosis without determining the cause of the stroke; and
   (b) administering to the person a composition comprising an amount of a pro-urokinase ("pro-UK") mutant M5 (Lys$^{300}$→His) polypeptide effective to lyse any potential blood clot causing the symptoms of stroke.

2. The method of claim 1, wherein the composition is administered more than 3 hours and up to 6 hours after the onset of symptoms.

3. The method of claim 1, wherein the composition is administered within 3 hours after the onset of symptoms.

4. The method of claim 1, wherein the composition is administered as a bolus of the composition comprising 20–50 mg of the pro-UK mutant M5 polypeptide.

5. The method of claim 1, further comprising obtaining a medical confirmation of an occlusive thrombus in the brain, and administering intravenously an infusion of the composition at a pro-UK mutant M5 polypeptide dosage of dose of 120–200 mg/hour.

6. The method of claim 1, further comprising obtaining a medical confirmation of an occlusive thrombus in the brain, and administering intra-arterially an infusion of the composition at a pro-UK mutant M5 polypeptide dosage of dose of 50–100 mg/hour.

* * * * *